(12) United States Patent
von Deyn et al.

(10) Patent No.: US 6,670,482 B2
(45) Date of Patent: Dec. 30, 2003

(54) PROCESS AND NOVEL INTERMEDIATES FOR PREPARING ISOXAZOLIN-3-YLACYL BENZENES

(75) Inventors: Wolfgang von Deyn, Neustadt (DE); Joachim Gebhardt, Wachenheim (DE); Michael Rack, Heidelberg (DE); Rene Lochtman, Mannheim (DE); Norbert Götz, Worms (DE); Michael Keil, Freinsheim (DE); Matthias Witschel, Ludwigshafen (DE); Helmut Hagen, Frankenthal (DE); Ulf Misslitz, Neustadt (DE); Ernst Baumann, Dudenhofen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/223,019

(22) Filed: Aug. 19, 2002

(65) Prior Publication Data

US 2003/0028033 A1 Feb. 6, 2003

Related U.S. Application Data

(62) Division of application No. 09/831,400, filed as application No. PCT/EP99/08746 on May 9, 2001, now Pat. No. 6,469,176.

(30) Foreign Application Priority Data

Nov. 12, 1998 (DE) .......................... 198 52 095
May 4, 1999 (EP) .................................. 03006

(51) Int. Cl.$^7$ ............................................ C07D 261/04
(52) U.S. Cl. ............................................. 548/240
(58) Field of Search ........................... 548/240

(56) References Cited

U.S. PATENT DOCUMENTS

| 6,124,469 A | * | 9/2000 | Rheinheimer et al. | ...... 548/240 |
| 6,359,143 B1 | | 3/2002 | Adachi et al. | ............... 548/247 |
| 6,469,176 B1 | * | 10/2002 | von Deyn et al. | .......... 548/240 |
| 6,525,204 B1 | | 2/2003 | Rheinheimer et al. | ...... 548/240 |

FOREIGN PATENT DOCUMENTS

WO  WO 99/64404  12/1999

OTHER PUBLICATIONS

Paradkar et al. "Reaction of β–Keto Ethyleneacetals with Hydroxylamine: A Correction" J. Heterocyclic Chem., 30, 1497–1500 (1993).

* cited by examiner

Primary Examiner—Joseph K. McKane
Assistant Examiner—Giolam MM Shameem
(74) Attorney, Agent, or Firm—Keil & Weinkauf

(57) ABSTRACT

The present invention describes a process for preparing isoxazoles of the formula I

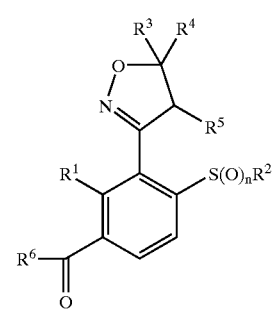

where:

$R^1$ is hydrogen, $C_1$–$C_6$-alkyl, $R^2$ is hydrogen, $C_1$–$C_6$-alkyl, $R^3$, $R^4$, $R^5$ are each hydrogen, $C_1$–$C_6$-alkyl or $R^4$ and $R^5$ together form a bond, $R^6$ is a heterocyclic ring, n is 0, 1 or 2;

which comprises preparing an intermediate of the formula VI

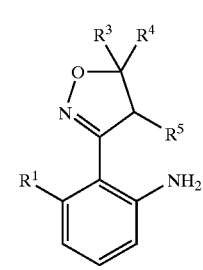

where $R^1$, $R^3$, $R^4$ and $R^5$ are each as defined above, followed by halogenation, thiomethylation, oxidation and acylation to give compounds of the formula I.

Furthermore, the invention describes novel intermediates for preparing the compounds of the formula I and novel processes for preparing the intermediates.

1 Claim, No Drawings

PROCESS AND NOVEL INTERMEDIATES FOR PREPARING ISOXAZOLIN-3-YLACYL BENZENES

This is a Divisional application of application Ser. No. 09/831,400, filed or May 9, 2001 U.S. Pat. No. 6,469,176 which is a 371 of PCT/EP99/08746 Nov. 12, 1999.

The present invention relates to a process for preparing isoxazolin-3-ylacylbenzenes, to novel intermediates and to novel processes for preparing these intermediates.

Isoxazolin-3-ylacylbenzenes are useful compounds which can be employed in the area of crop protection. 2-Alkyl-3-(4,5-dihydro-isoxazol-3-yl)acylbenzenes are described, for example, in WO 98/31681, as herbicidally active compounds.

It is an object of the present invention to provide an alternative process for the preparation of 3-heterocyclyl-substituted benzoyl derivatives described in WO 98/31681. The process described in WO 98/31681 for preparing the 2-alkyl-3-(4,5-dihydroisoxazol-3-yl)acylbenzenes and their precursor (2-alkyl-3-(4,5-dihydroisoxazol-3-yl) bromobenzene derivatives) is not well suited for the preparation of these compounds on a large industrial scale, since the synthesis extends over several steps and the yield of the respective end product is relatively low, based on the starting materials employed in the first step of the synthesis.

We have found that this object is achieved by reducing the number of process steps required for preparing the 3-heterocyclyl-substituted benzoyl derivatives, compared with the process described in WO 98/31681, when the synthesis occurs via selected intermediate compounds. Moreover, the process according to the invention has the advantage that the overall yield of end products of the formula I and also for the intermediates, based on the starting materials employed, is higher than the yield in the processes described in WO 98/31681. In addition, the respective intermediates in the individual process steps can be obtained in good yield. Moreover, some of the individual process steps are advantageous for the industrial preparation of the intermediate compounds since they allow a cost-effective and economical preparation of these compounds. It is furthermore advantageous that the starting materials used are basic chemicals which are easy to prepare and which can be obtained from a number of independent suppliers of basic chemicals, even in relatively large amounts. Altogether, the process according to the invention provides a cost-effective, economical and safe industrial-scale process for preparing herbicidally active compounds of the formula I.

The present invention provides a process for preparing the compounds of the formula I

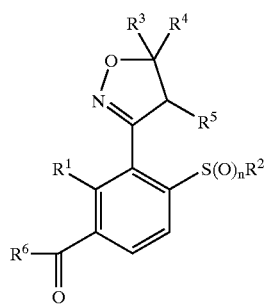

I where:

$R^1$ is hydrogen, $C_1$–$C_6$-alkyl,
$R^2$ is hydrogen, $C_1$–$C_6$-alkyl,
$R^3$, $R^4$, $R^5$ are each hydrogen, $C_1$–$C_6$-alkyl or $R^4$ and $R^5$ together form a bond,
$R^6$ is a heterocyclic ring,
n is 0, 1 or 2;

which comprises preparing an intermediate of the formula VI,

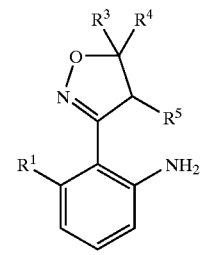

VI in which $R^1$, $R^3$–$R^5$ are each as defined above.

In subsequent reaction steps, compounds of the formula VI are converted into the corresponding 3-bromo-substituted compounds (bromobenzene derivatives), and the amino group at the phenyl ring is converted into an $S(O)_nR^2$ group, preferably sulfonyl group, giving rise to compounds of the formula X:

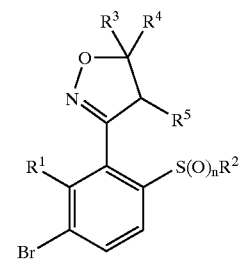

X

The compounds of the formula X (3-(4,5-dihydroisoxazol-3-yl)bromobenzenes) are useful intermediates for preparing active compounds of the formula I. In particular, the process according to the invention gives the compounds I in the last reaction step in good yield. The compounds I are suitable, for example, for use as crop protection agents, in particular as herbicides, as described in WO 96/26206 and WO 97/35850.

The present invention particularly preferably provides a process for preparing the compounds of the formula I where $R^2$=$C_1$–$C_6$-alkyl, which comprises preparing an intermediate of the formula VI.

The present invention likewise particularly preferably provides a process for preparing compounds of the formula I where $R^2$=hydrogen, comprising the preparation of an intermediate of the formula VI.

Likewise according to the invention, it is possible to prepare compounds of the formula I or the intermediates required for this, in particular compounds of the formula VI or X, in an advantageous manner by combining one or more of the following process steps a)–g), where, with respect to the compounds of the formula I, one process step of the group of process steps a)–f) has to be, involved:

a) reaction of a nitro-o-methylphenyl compound of the formula II

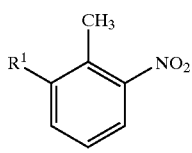

in which the radical $R^1$ is as defined above, with an organic nitrite R-ONO under action of a base to give the oxime of the formula III

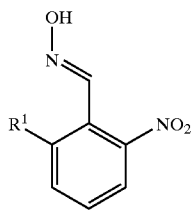

in which the radical $R^1$ is as defined above;
b) cyclization of the oxime of the formula III using an alkene of the formula IV

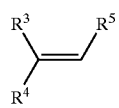

in which $R^3$ to $R^5$ are each as defined in claim 1, in the presence of a base to give the isoxazole of the formula V

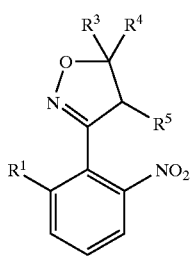

in which $R^1$, $R^3$ to $R^5$ are each as defined in claim 1;
c) reduction of the nitro group in the presence of a catalyst to give the aniline of the formula VI

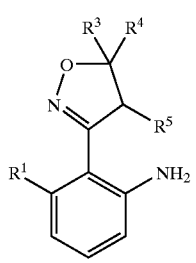

in which $R^1$, $R^3$ to $R^5$ are each as defined in claim 1;
d) reaction of the aniline of the formula VI with a dialkyl disulfide of the formula VII

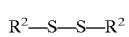

in the presence of an organic nitrite R-ONO and, if appropriate, a catalyst to give the thioether of the formula VIII

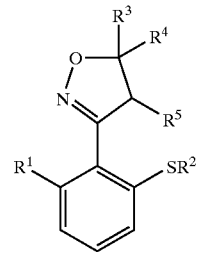

in which $R^1$ to $R^5$ are each as defined in claim 1;
e) bromination of the thioether of the formula VIII with a brominating agent to give the bromothioether of the formula IX

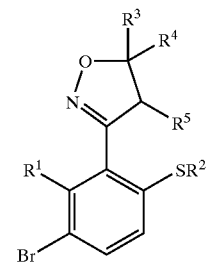

in which $R^1$ to $R^5$ are each as defined in claim 1;
f) oxidation of the bromothioether of the formula IX with an oxidizing agent to give the isoxazole of the formula X

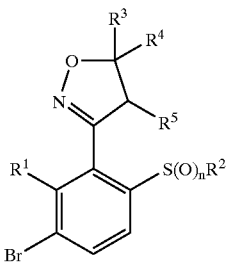

where n is the number 1 or 2,
g) if appropriate, reaction of the isoxazoline of the formula X with a compound of the formula $R^6$—OH (XI) in the presence of carbon monoxide, a catalyst and a base to give the compounds of the formula I.

The process according to the invention for preparing compounds X comprises essentially one or more of the process steps a)–f) or, in the case of the compounds I, one or more of the process steps a)–g), where a process step from the group of process steps a)–f) has to be involved. Preference is given to reaction sequences which comprise either one of process steps a) or d) or else both steps a) and d).

In all cases, $C_1$–$C_6$-alkyl and $C_1$–$C_4$-alkyl are straight-chain or branched alkyl groups having 1–6 and 1–4 carbon atoms, respectively, such as, for example, methyl, ethyl, n-propyl, isopropyl, n-butyl, isobutyl, n-pentyl or n-hexyl. This applies analogously to the $C_1$–$C_6$-alkoxy group.

$R^1$, $R^2$ are preferably alkyl groups, in particular methyl, ethyl, isopropyl, n-propyl or n-butyl groups.

$R^3$, $R^4$ and $R^5$ are preferably hydrogen. $R^4$ and $R^5$ together may also represent a bond, resulting in the corresponding isoxazole derivatives. In this case, $R^3$ is preferably hydrogen.

In the definition of $R^6$, "heterocyclic ring" is a saturated, unsaturated or partially unsaturated heterocycle having 1, 2 or 3 oxygen, sulfur or nitrogen atoms. Preference is given to heterocycles having two nitrogen atoms. In particular, $R^6$ is a pyrazole radical as described in more detail in WO 98/31681. It is preferably a pyrazole attached in the 4-position which may be unsubstituted or substituted by further radicals which are chemically inert under the chosen reaction conditions. Such suitable pyrazole substituents are, for example, the following groups: hydroxyl, oxo, sulfonyloxy, $C_1$–$C_6$-alkyl or $C_1$–$C_6$-alkoxy, in particular in the 1-position $C_1$–$C_4$-alkyl. $R^6$ is particularly preferably the group 1-alkyl-5-hydroxypyrazol-4-yl, in particular 1-methyl-5-hydroxypyrazol-4-yl; 1-ethyl-5-hydroxypyrazol-4-yl.

The process according to the invention is particularly suitable for preparing the following compounds of the formula I:

1-methyl-4-(3-(4,5-dihydroisoxazol-3-yl)-2-methyl-4-methyl-sulfonylbenzoyl)-5-hydroxypyrazole,
1-ethyl-4-(3-(4,5-dihydroisoxazol-3-yl)-2-methyl-4-methyl-sulfonylbenzoyl)-5-hydroxypyrazole,
1-methyl-4-(3-(4,5-dihydroisoxazol-3-yl)-2-ethyl-4-methyl-sulfonylbenzoyl)-5-hydroxypyrazole,
1-methyl-4-(3-(4,5-dihydroisoxazol-3-yl)-2-propyl-4-methyl-sulfonylbenzoyl)-5-hydroxypyrazole,
1-methyl-4-(3-(4,5-dihydroisoxazol-3-yl)-2-butyl-4-methyl-sulfonylbenzoyl)-5-hydroxypyrazole.

Preferred intermediates of the formula VI are the following compounds:

2-(4,5-dihydroisoxazol-3-yl)aniline,
2-(4,5-dihydroisoxazol-3-yl)-3-methylaniline,
2-(4,5-dihydroisoxazol-3-yl)-3-ethylaniline,
2-(Isoxazol-3-yl)aniline,
2-(isoxazol-3-yl)-3-methylaniline,
2-(isoxazol-3-yl)-3-ethylaniline.

The process according to the invention is particularly suitable for preparing the following intermediates of the formula X:

3-(3-bromo-2-methyl-6-methylsulfonylphenyl)-4,5-dihydroisoxazole,
3-(3-chloro-2-methyl-6-methylsulfonylphenyl)-4,5-dihydroisoxazole,
3-(3-bromo-6-methylsulfonylphenyl)-4,5-dihydroisoxazole,
3-(3-bromo-2-ethyl-6-methylsulfonylphenyl)-4,5-dihydroisoxazole,
3-(3-bromo-2-isopropyl-6-methylsulfonylphenyl)-4,5-dihydroisoxazole,
3-(3-bromo-2-methyl-6-ethylsulfonylphenyl)-4,5-dihydroisoxazole,
3-(3-bromo-2-methyl-6-propylsulfonylphenyl)-4,5-dihydroisoxazole,
3-(3-bromo-2-methyl-6-butylsulfonylphenyl)-4,5-dihydroisoxazole,
3-(3-bromo-2-methyl-6-pentylsulfonylphenyl)-4,5-dihydroisoxazole,
3-(3-bromo-2-methyl-6-hexylsulfonylphenyl)-4,5-dihydroisoxazole.

A possible reaction sequence up to the preparation of the compounds X is summarized in the synoptical diagram below:

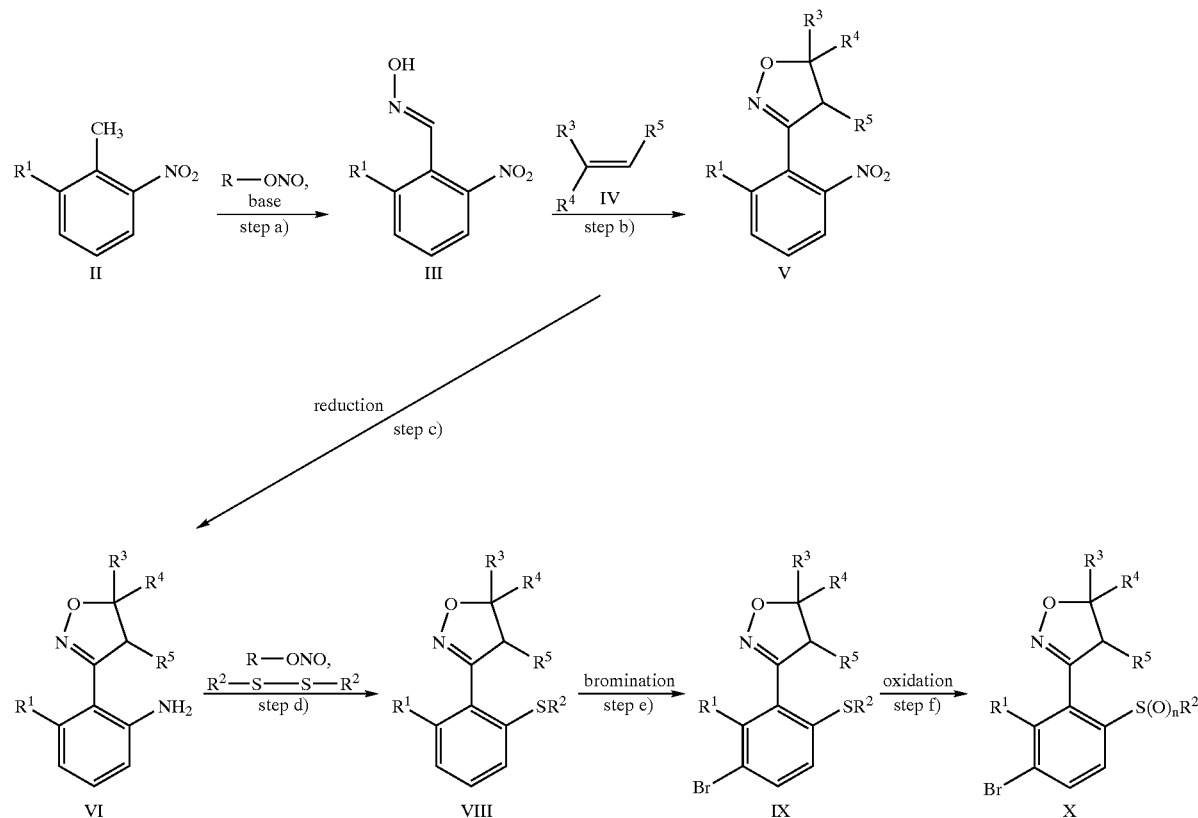

Hereinbelow, the individual reaction steps are briefly illustrated in more detail.

1. Step a)

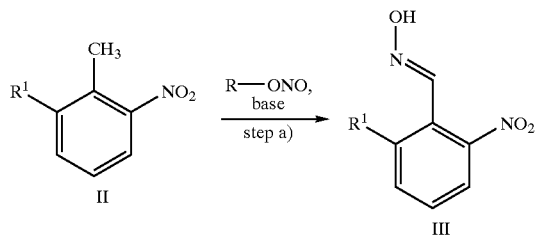

The reaction is carried out, for example, under the following conditions: the solvents used are bipolar aprotic solvents, for example N,N-dialkylformamide, N,N-dialkylacetamide, N-methylpyrrolidone (NMP), preferably: dimethylformamide (DMF) or NMP. The temperature is from −60° C. to room temperature; preferably from −50 to −20° C.; especially preferably from −35 to −25° C. To achieve a sufficient low melting point of the solvent system, it is also possible to use mixtures of solvents, such as, for example, with THF. The organic nitrites R—ONO used are alkyl nitrites (R=alkyl), preferably n-butyl nitrite or (iso) amyl nitrite. Suitable bases are: MOalkyl, MOH, RMgX (M=alkali metal); preferably potassium methoxide (KOMe), sodium methoxide (NaOMe) or potassium tert-butoxide (KOtbutoxide). When using sodium bases, 1–10 mol % of amyl alcohol may be added, if appropriate. The stoichiometric ratios are, for example, as follows: 1–4 equivalents of base, 1–2 equivalents of R—ONO; preferably 1.5 –2.5 equivalents of base and 1–1.3 equivalents of R—ONO; equally preferably: 1–2 equivalents of base and 1–1.3 equivalents of R—ONO.

The addition is carried out, for example, according to the following metering sequence: a) nitro-o-xylene and nitrite are initially charged and the base is metered in. b) To avoid having to meter in the solid base, the base can initially be charged in DMF, and nitro-o-xylene/butyl nitrite can be added simultaneously. The metering rate for adding the base is relatively slow, so that the cooling required is reduced to a minimum. Work-up is carried out by one of the following methods: a) precipitation of the product by stirring the mixture into water or into a mineral acid/water mixture such as, for example, hydrochloric acid/water. b) Precipitation of the product by addition of a sufficient amount of water to the reaction mixture. The product is purified by extraction with toluene at from 0 to 110° C., preferably at room temperature.

2. Step b)

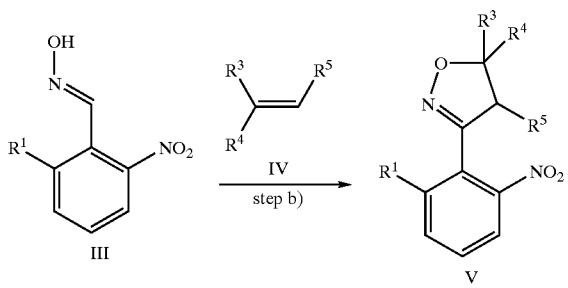

The reaction is carried out, for example, via the following mechanistic intermediates: conversion of the oxime III into an activated hydroxamic acid derivative, such as, for example, hydroxamic acid chloride, by chlorination with a chlorinating agent, conversion of the activated hydroxamic acid derivative into the nitrile oxide, such as, for example, conversion of the hydroxamic acid chloride in the presence of a base into the nitrile oxide, and subsequent cycloaddition of the alkene IV to the nitrile oxide.

This reaction is a novel process for preparing isoxazole derivatives of the formula V. Surprisingly, this process affords the isoxazalines is very good yields. Furthermore, only a few by-products are formed which, moreover, can also be removed relatively easily. Owing to this, it is possible to isolate and purify the end products in a simple manner on a large industrial scale, so that the isoxazolines can be prepared in high purity and at low cost. Hitherto, the use of known processes for preparing isoxazolines has been disadvantageous, since the isoxazalines could be obtained from the reaction of the benzaldoximes only in unsatisfactory yields. Furthermore, the processes known from the prior art frequently make use of alkali metal hypohalide-containing solutions which lead to the formation of poorly soluble and environmentally unfriendly by-products. The process according to the invention is characterized in that the use of alkali metal hypohalite-containing solutions can be dispensed with, the process thus being essentially free of alkali metal hypohalites.

The isoxazolines are prepared, for example, by the following method: initially, hydroxamic acid chloride is formed which is cyclized in a second step with an alkene, if appropriate at superatmospheric pressure, and with metered addition of base. These individual steps can also be combined in an advantageous manner in a "one-pot reaction". To this end, a solvent is employed in which both partial steps proceed, for example carboxylic esters, such as ethyl acetate, chlorobenzene or acetonitrile.

The preparation of hydroxamic acid chlorides using N-chlorosuccinimide in DMF is known from the literature (Liu et al., J. Org. Chem. 1980, 45: 3916–3918). However, it is also mentioned that the conversion of o-nitrobenzaldoximes into the hydroxamic acid chlorides by chlorination gives only poor yields (Chiang, J. Org. Chem. 1971, 36: 2146–2155). The formation of benzal chloride is to be expected as a side reaction. Surprisingly, in accordance with the process described above, we have found conditions which permit preparation of the desired hydroxamic acid chlorides in excellent yields. Particularly advantageous is the use of the inexpensive chlorine.

The reaction is carried out, for example, under the following conditions: solvents: haloalkanes, such as 1,2-dichloroethane or methylene chloride; aromatics, such as benzene, toluene, chlorobenzene, nitrobenzene or xylene; polar aprotic solvents, for example N,N-dialkylformamides, -acetamides, N-methylpyrrolidone, dimethylpropylene urea; tetramethyl urea, acetonitrile, propionitrile; alcohols, such as methanol, ethanol, n-propanol or isopropanol; carboxylic acids, such as acetic acid or propionic acid; carboxylic esters, such as ethyl acetate. Preference is given to using the following solvents: acetic acid, methanol, ethanol, 1,2-dichloroethane, methylene chloride or chlorobenzene or ethyl acetate. The reaction is carried out at from −40° C. to 100° C.; preferably from −10 to 40° C. or from 0 to 30° C.; the reaction is equally preferably carried out in a temperature range of 30–60° C., in particular 30–50° C. Suitable halogenating agents are: N-chlorosuccinimide, elemental chlorine, preferably chlorine. The stoichiometric ratios are, for example, 1–3 equivalents of halogenating agent, preferably 1–1.5 equivalents. The metered addition is carried out, in the case of chlorine, by passing the gas through the solution, in the case of N-chlorosuccinimide (NCS) by addition as a solid or, if appropriate, in a suitable solvent.

Work-up is carried out, for example, according to the following scheme: a) without purification. The solution is employed for the next step; b) solvent exchange by distillative removal of the solvent; c) addition of water and extraction of the hydroxamic acid chloride using a suitable solvent.

By addition of bases, the hydroxamic acid chlorides are converted into the nitrile oxides. Since these compounds are unstable, the object which had to be achieved was finding conditions which permit stabilization of the nitrile oxides, and their conversion into the desired products. Surprisingly, this object can be achieved by choosing the reaction conditions below: the solvents used are: haloalkanes, such as 1,2-dichloroethane or methylene chloride; aromatics, such as benzene, toluene, chlorobenzene, nitrobenzene or xylene; polar aprotic solvents, for example, N,N-dialkylformamides, -acetamides, N-methylpyrrolidone, dimethylpropylene urea; tetramethyl urea, acetonitrile, propionitrile, carboxylic esters, such as ethyl acetate. Preference is given to using: 1,2-dichloroethane, methylene chloride, toluene, xylene, ethyl acetate or chlorobenzene.

The temperatures for the reaction are from 0° C. to 100° C., preferably from 0 to 50° C. or from 0 to 30° C.

The bases employed are: tertiary amines, for example triethylamine, cyclic amines, such as N-methylpiperidine or N,N'-dimethylpiperazine, pyridine, ammonia, alkali metal carbonates, for example sodium carbonate or potassium carbonate, alkali metal bicarbonates, for example sodium bicarbonate or potassium bicarbonate, alkaline earth metal carbonates, for example calcium carbonate, alkali metal hydroxides, for example sodium hydroxide or potassium hydroxide. Preference is given to using: triethylamine, sodium carbonate, sodium bicarbonate or sodium hydroxide.

The stoichiometric ratios are, for example, 1–3 equivalents of base, preferably 1–1.5 equivalents, equally preferably 2 to 3 equivalents; 1–5 equivalents of alkene, preferably 1–2 equivalents. The metered addition is preferably carried out under a superatmospheric alkene pressure, by slowly adding the base. The reaction is carried out at from atmospheric pressure to 10 atm, preferably 0–6 atm atmospheric pressure.

3. Step c)

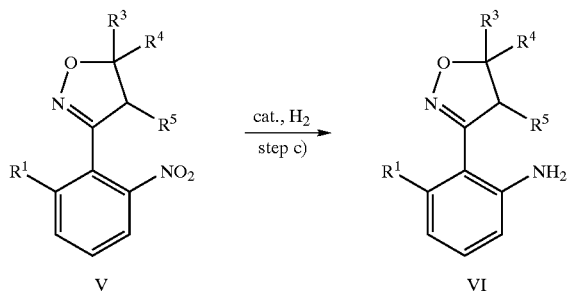

This reaction is a novel chemoselective hydrogenation of a nitro group in the presence of an isoxazoline, said reaction having hitherto been unknown. Surprisingly, it has been found that the N—O bond of the isoxazoline is not cleaved under the chosen reaction conditions. The catalytic hydrogenation of aromatic nitro compounds to anilines has been known for a long time (see Houben Weyl, Vol. IV/1c, p. 506 ff). On the other hand, it has also been known that the N—O bond of isoxazolines can be cleaved by catalytic hydrogenation, for example using Raney-Nickel (Curran et al., Synthesis 1986, 312–315) or palladium (Auricchio et al., Tetrahedron, 43 (1987), 3983–3986) as catalyst.

The reaction is carried out, for example, under the following conditions: suitable solvents are aromatics, such as benzene, toluene, xylene; polar aprotic solvents, for example N,N-dialkylformamides, -acetamides, N-methylpyrrolidone, dimethylpropylene urea; tetramethyl urea, carboxylic esters, such as ethyl acetate, ethers, such as diethyl ether or methyl tert-butyl ether, cyclic ethers, such as tetrahydrofuran or dioxane; alcohols, such as methanol, ethanol, n-propanol, isopropanol or n-butanol, carboxylic acids, such as acetic acid or propionic acid. Preference is given to using the following solvents: ethyl acetate, toluene, xylene, methanol, ethanol or dimethylformamide; in particular methanol or dimethylformamide. The reaction is carried out at from −20° C. to 100° C.; preferably from 0 to 50° C., particularly preferably from 0 to 30° C. The reaction is equally preferably carried out in a temperature range of 30–40° C. The catalyst used is a platinum or palladium catalyst supported on activated carbon, having a content of from 0.1 to 15% by weight, based on the support of an activated carbon. If a palladium catalyst is employed, this catalyst can be doped with sulfur or selenium to achieve better selectivity. Preference is given to using platinum/activated carbon or palladium/activated carbon having a content of Pt or Pd of from 0.5 to 10% by weight.

The stoichiometric ratios for the reaction are, for example, as follows: from 0.001 to 1% by weight of platinum or palladium, based on the nitro compound; preferably from 0.01 to 1% by weight of platinum, equally preferably 0.01 to 1% by weight of palladium. The metered addition of hydrogen is carried out continuously or batchwise, preferably batchwise at from atmospheric pressure to 50 atm, preferably at atmospheric pressure to 20 atm, particularly preferably atmospheric pressure to 10 atm.

Work-up of the reaction mixture is carried out by removing the catalyst by filtration. If appropriate, the catalyst can be recycled. The solvent is distilled off. For the subsequent reaction in the next process step, the product can be used directly without further purification. If required, it is also possible to purify the product further. The product is purified, for example, according to the following scheme: if required, the aniline can be purified by taking up the residue in dilute mineral acid, for example aqueous hydrochloric acid or dilute sulfuric acid, extraction with a suitable organic extractant, for example haloalkanes, such as 1,2-dichloroethane or methylene chloride, aromatics, such as benzene, toluene, chlorobenzene or xylene, ethers, such as diethyl ether or methyl tert-butyl ether, carboxylic esters, such as ethyl acetate, and be liberated again using a base.

4. Step d)

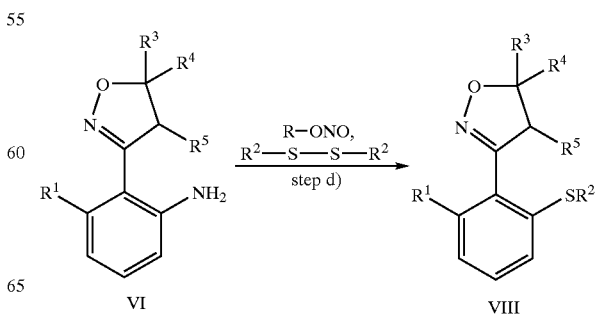

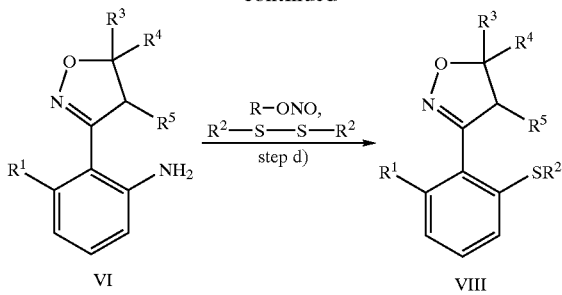

The reaction is carried out for compounds of the formula VIII where $R^2=C_1-C_6$-alkyl under the following conditions: suitable solvents are, for example: haloalkanes, such as 1,2-dichloroethane or methylene chloride, aromatics, such as benzene, toluene, chlorobenzene, nitrobenzene, or an excess of the dialkyl disulfide as solvent. Preference is given to using an excess of the dialkyl disulfide as solvent. The temperature for the reaction is from 40° C. to 150° C.; preferably from 50 to 100° C., particularly preferably from 60 to 90° C. The reaction is carried out equally well in a temperature range of 45–75° C., in particular in a range of 55–65° C. The reagents used are organic nitrites (R—ONO), such as, for example, alkyl nitrites, preferably n-butyl nitrite, (iso)amyl nitrite or tert-butyl nitrite. Here, R can be any organic radical which is chemically inert and has no effect on the actual reaction. R is, for example, a $C_1-C_6$-alkyl or $C_2-C_6$-alkenyl group.

The stoichiometric ratios in the reaction of the compounds are, for example, as follows: 1–3 equivalents of alkyl nitrite, preferably 1–1.5 equ. of alkyl nitrite, especially preferably 1–1.3 equ. of alkyl nitrite. Suitable catalysts are: copper powder, elemental copper in a different form, such as, for example, turnings, wire, granules, shot, rods; copper(I) salts, for example copper(I) chloride, copper(I) bromide or copper (I) iodide, copper(II) salts, or elemental iodine, particularly preferably copper powder, likewise particularly preferably copper salts. When carrying out the reaction in a solvent, 1–3 equivalents of dialkyl disulfide, preferably 1–2 equivalents, are employed. In a preferred embodiment, an excess of dialkyl disulfide is employed as solvent, which is subsequently recovered by distillation. For further conversion, the product can be used without further purification. If required, it is also possible to purify the product beforehand, by distillation or crystallization with the aid of suitable solvents, such as, for example, from diisopropyl ether.

Usually, the dialkyl disulfide, the organic nitrite and the catalyst are initially charged and the compound of the formula VI and further dialkyl disulfide are metered in. However, it is also possible to initially charge the compound of the formula VI, the dialkyl disulfide and the catalyst and to meter in the organic nitrite.

Compounds of the formula VIII where $R^2$=hydrogen are obtained similarly to processes known from the literature, for example by diazotizing the compound of the formula VI in aqueous medium with a nitrite or in organic or aqueous/organic medium with an organic nitrite (R—ONO) and reacting the diazonium salt with a metal sulfide, in particular an alkali metal sulfide, such as sodium sulfide. It is also possible to react the diazonium salt with a xanthogenate, such as, for example, potassium ethylxanthogenate, and then to hydrolyze the aryl xanthogenate formed to give the compound VIII where $R^2$=hydrogen. Suitable for this purpose are, inter alia, ammonia, sodium hydroxide or potassium hydroxide, in particular ethanolic potassium hydroxide solution (Houben-Weyl, Vol. 9, p. 12, 4th edition).

5. Step e)

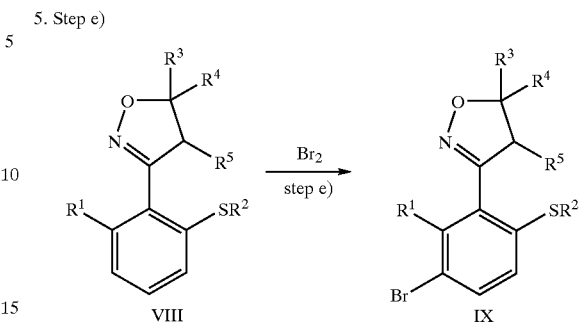

The bromination is carried out similarly to the method described in WO 98/31676. Advantageously, the solvent used is acetic acid.

6. Step f)

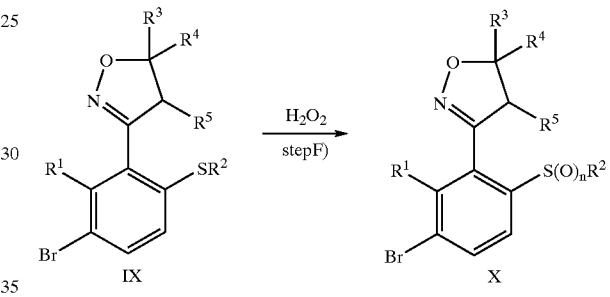

The oxidation is carried out similarly to the method described in WO 98/31676 (cf. p. 8 line 32 to p. 11, line 25).

7. Step g)

The conversion of the compound of the formula X into compounds of the formula I, which is carried out subsequently, if appropriate, is carried out by addition of $R^6$—OH (XI) in the presence of carbon monoxide and a suitable catalyst and a base. If $R^6$ is an unsubstituted or substituted pyrazole or pyrazoline ring, the reaction is preferably carried out using palladium-containing catalysts, such as, for example, Pd(O) catalyst or bis-triphenylphosphine-palladium(II) chloride The process is illustrated hereinbelow in more detail using the example where $R^6$=pyrazole (XI.a) as heterocycle. In principle, however, it is also possible to use other heterocyclic compounds, such as defined initially.

The process is preferably carried out by reacting a hydroxypyrazole of the formula XI.a XI.a

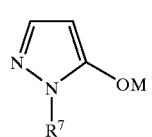

in which $R^7$ is $C_1$–$C_6$-alkyl and M is hydrogen or an alkali metal atom, preferably sodium or potassium, with a bromobenzene of the formula X

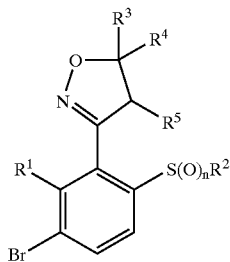

in which $R^1$ to $R^5$ are as defined above, in the presence of carbon monoxide, a palladium catalyst, if appropriate at least one molar equivalent of a potassium salt and, if appropriate, at least one molar equivalent of a tertiary amine of the formula XIII

                        XIII in which one of the radicals $R_a$ may represent phenyl or naphthyl and the other radicals $R_a$ are $C_1$–$C_6$-alkyl, at temperatures of from 100 to 140° C. and at a pressure of from 1 to 40 kg/cm².

In a preferred embodiment of the process, the 5-hydroxypyrazole XI.a and the bromobenzene derivative X are employed in a molar ratio of from 1 to 2.

The 5-hydroxypyrazoles XI.a used are preferably compounds in which $R^7$ is $C_1$–$C_6$-alkyl, in particular methyl or ethyl.

The 5-hydroxypyrazoles (or pyrazolinones) of the formula XI.a used as starting materials are known and can be prepared by processes known per se (cf. EP-A 240 001, WO 96/26206 and J. Prakt. Chem. 315 (1973), p. 382).

In general, the 5-hydroxypyrazole XI.a is employed in equimolar amounts or in excess, based on the bromobenzene derivative X. For economical reasons, it is expedient to avoid a large excess of 5-hydroxypyrazole. Under the reaction conditions according to the invention, a stoichiometric reaction gives the same yield as when an excess of 5-hydroxypyrazole is used. This was surprising, since in all of the examples for the process described in EP-A 344 775, a large excess of 5-hydroxypyrazole is used. In the process according to the invention, the molar ratio of 5-hydroxypyrazole to bromobenzene is preferably set to from 1 to 2 and particularly preferably to from 1.0 to 1.2.

Above 140° C., decomposition occurs, below 100° C., the reaction comes to a standstill. Thus, in general, the reaction is carried out in a temperature range of from 100 to 140° C. and preferably from 110 to 130° C.

The reaction is usually carried out at a pressure of at most up to 40 kg/cm², preferably up to 20 kg/cm² or else up to 10 kg/cm² without this having an adverse effect on the reaction conditions, such as reaction temperature or reaction time, or resulting in a loss of yield. The reaction pressure is preferably at least 3 kg/cm², in particular at least 5 kg/cm². Exemplary pressure ranges are: 1–40 kg/cm², 5–20 kg/cm² or 10–20 kg/cm², in particular 3–10 and particularly preferably 5–8 kg/cm².

This pressure reduction is particularly advantageous for the industrial-scale preparation process, since the safety requirements which have to be met with respect to the pressure vessels used can be reduced. The cost-intensive use of high-pressure containers can thus be dispensed with.

Under the chosen process conditions, most of the palladium compounds used as catalyst are obtained as elemental palladium, and they can be removed from the reaction mixture is a simple manner by filtration. Thus, concentration of the palladium-containing reaction solution for subsequent disposal and any incineration of residues, which is complicated from a technical point of view and involves high costs, can substantially be dispensed with. Because of this, recycling costs are reduced. The pore size of the precipitated palladium is 1–10 μm, in particular 1–4 μm. At lost costs, the palladium removed by filtration can be worked up to the corresponding palladium compounds, such as, for example, palladium chloride, since the recycling costs depend on the concentration of the palladium.

Suitable solvents for the reaction in process step g) are nitrites, such as benzonitrile and acetonitrile, amides, such as dimethylformamide, dimethylacetamide, tetra-$C_1$–$C_4$-alkylureas or N-methylpyrrolidone and preferably ethers, such as tetrahydrofuran, methyl tert-butyl ether. Particularly preferred solvents are ethers such as 1,4-dioxane and dimethoxyethane.

Suitable catalysts are palladium ligand complexes in which the palladium is present in oxidation state 0, metallic palladium, if appropriate on a support, and preferably palladium(II) salts. The reaction with palladium(II) salts and metallic palladium is preferably carried out in the presence of complex ligands.

A suitable palladium(0) ligand complex is, for example, tetrakis(triphenylphosphine)palladium.

Metallic palladium is preferably deposited on an inert support, such as, for example, activated carbon, silica, alumina, barium sulfate or calcium carbonate. The reaction is preferably carried out in the presence of complex ligands, such as, for example, triphenylphosphine.

Suitable palladium(II) salts are, for example, palladium acetate and palladium chloride. The reaction is preferably carried out in the presence of complex ligands, such as, for example, triphenylphosphine.

Suitable complex ligands for the palladium ligand complexes, or those, in the presence of which the reaction with metallic palladium or palladium(II) salts is preferably carried out, are tertiary phosphines, whose structure is represented by the formulae below:

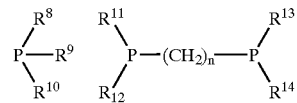

where n denotes the numbers 1 to 4 and the radicals $R^8$ to $R^{14}$ are $C_1$–$C_6$-alkyl, aryl-$C_1$–$C_2$-alkyl or, preferably, aryl. Aryl is, for example, naphthyl and unsubstituted or substituted phenyl, such as, for example, 2-tolyl, and in particular unsubstituted phenyl.

The complex palladium salts can be prepared in a manner known per se from commercially available palladium salts, such as palladium chloride or palladium acetate, and the corresponding phosphines, such as, for example, triphenylphosphine or 1,2-bis(diphenylphosphino)ethane. Many complex palladium salts are also commercially available. Preferred palladium salts are [(R)(+)-2,2'-bis(diphenylphosphino)-1,1'-binaphthyl]palladium(II) chloride, bis(triphenylphosphine)palladium(II) acetate and, in particular, bis(triphenylphosphine)palladium(II) chloride.

The palladium catalyst is generally employed in a concentration of from 0.05 to 5 mol % and preferably 1–3 mol %.

Amines $N(R_a)_3$ of the formula XIII which are suitable for the process are tertiary amines, such as, for example, N-methylpiperidine, ethyldiisopropylamine, 1,8-bisdimethylaminonaphthalene or, in particular, triethylamine, and also trimethylamine.

Suitable potassium salts are, for example, potassium phosphate, potassium cyanide and, in particular, potassium carbonate. Advantageously, the water content of the potassium salt should be low. Accordingly, the potassium carbonate was generally dried at least 150° C. prior to use.

The amount of potassium salt used is advantageously at least 1 molar equivalent. Otherwise, the reaction proceeds more slowly and/or the intermediate Fries rearrangement does not go to completion, giving O-acylated pyrazole derivatives. Preference is given to using in each case from 2 to 4 molar equivalents and particularly preferably 2 molar equivalents of potassium salt, based on bromobenzene III.

In addition to the potassium salt, the reaction mixture is also admixed with an amine $N(R_a)_3$ of the formula XIII in which one of the radicals $R_a$ is phenyl or naphthyl and the other radicals $R_a$ are $C_1$–$C_6$-alkyl. Preference is given to using from 1 to 4 molar equivalents, particularly preferably 2 molar equivalents, of the amine XIII, based on bromobenzene X.

For work-up, the reaction solution is generally introduced into water. If the reaction is carried out in a water-miscible solvent, such as 1,4-dioxane, it may be advantageous to remove some or all of the solvent from the reaction mixture beforehand, if appropriate under reduced pressure. Any solid components present are removed from the aqueous alkaline reaction mixture, and the pH is then adjusted to 2.0–4.5, preferably from 2.5–4.5, particularly preferably 3.5, by acidification with a mineral acid, such as, for example, hydrochloric acid or sulfuric acid, resulting in virtually complete precipitation of the product of value. The isoxazoline radical, in particular, is sensitive to hydrolysis. In processes for preparing benzoylpyrazoles carrying this radical, a pH of below 2 is advantageously to be avoided.

For the acylation in process step g), the following process conditions are preferably chosen: solvent: dioxane or mixtures of dioxane and acetonitrile. Temperature: 110–130° C. Pressure: 5–8, preferably about 6, kg/cm². Catalyst: palladium(II) chloride. Molar ratio of heterocyclic hydroxyl compounds (such as, for example, 5-hydroxypyrazole) to bromobenzene derivatives: 1–2, particularly preferably 1.0–1.2.

Alternatively to the synthesis route shown in scheme 1, the compounds of the formula X can also be prepared according to scheme 2 or 3 below.

Scheme 2 shows a possible synthesis route to the bromobenzene derivatives of the type of formula X using the synthesis of 3-[3-bromo-2-methyl-6-(methylsulfonyl)phenyl]-4,5-dihydroisoxazole as an example. The individual process steps can be carried out similarly to customary standard methods.

Scheme 2:

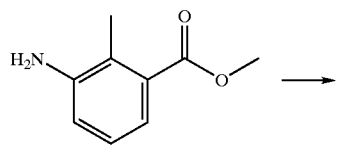

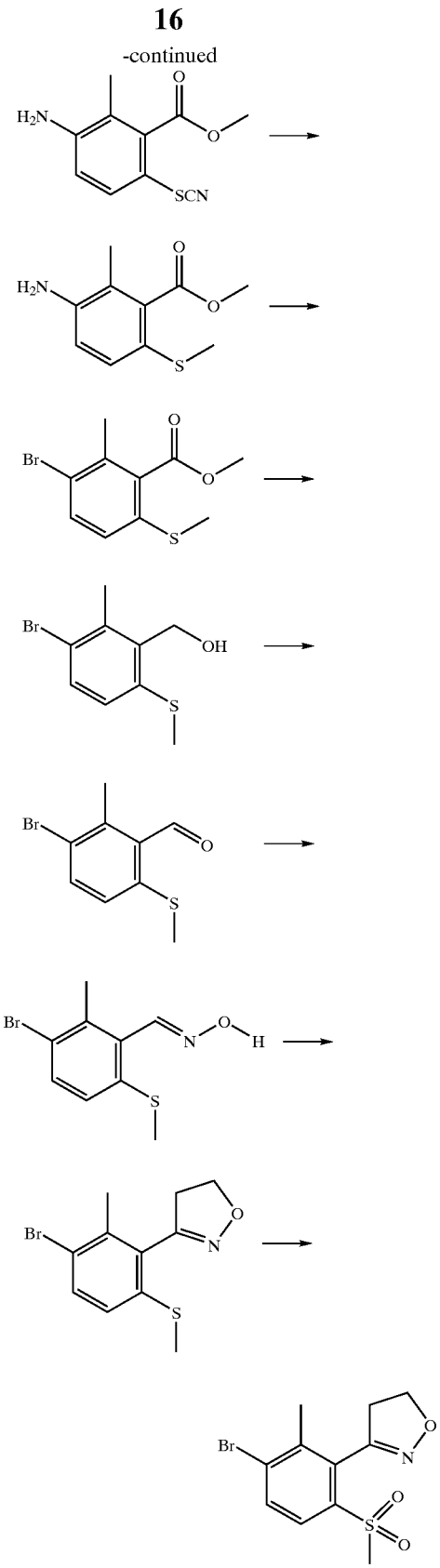

Scheme 3 shows a further possible synthesis route to the bromobenzene derivatives of the type of formula X Scheme 3:

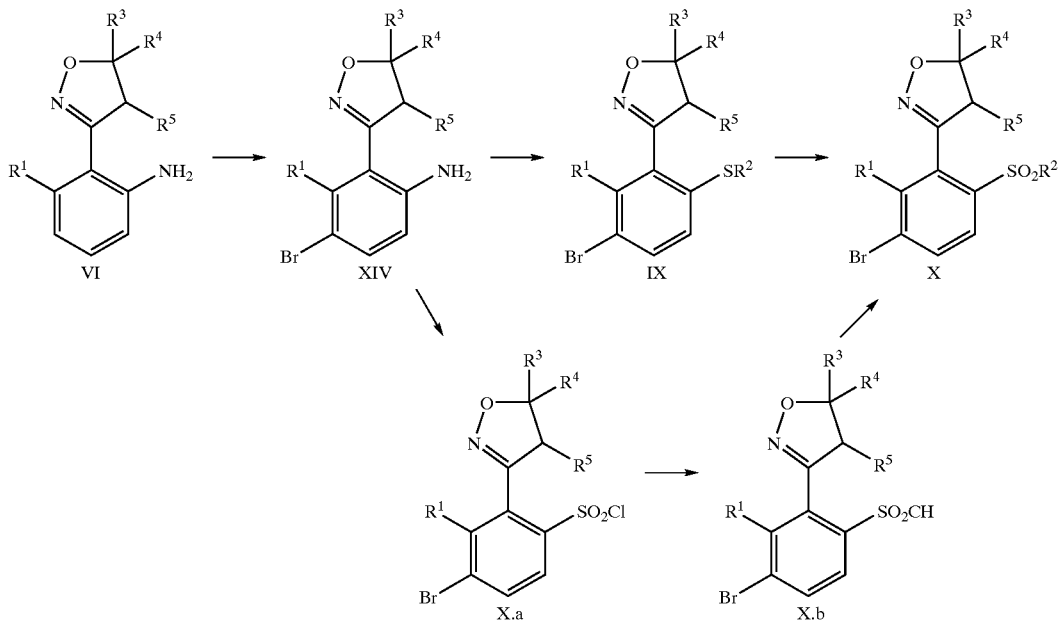

The bromination of compounds of the formula VI is carried out in a manner similar to the direct bromination of anilines. If the reagent used is tetrabutylammonium tribromide, a selective monobromination in the para position to the amino function can be achieved in some cases (Berthelot et al., Synth. Commun. 16 (1986), 1641). However, a general problem of such brominations is the formation of polybrominated products (Bull. Chem. Soc. Jpn. 61 (1988), 597–599). If, for example, the reaction of VI with tetrabutylammonium tribromide is carried out in a mixture of water and methanol, using calcium carbonate as base, a product mixture is obtained which contains approximately 25% of dibrominated by-product. Separation of the product mixture is critical in particular if the substituents present include isoxazole and/or isoxazoline radicals which, under the chosen reaction conditions, are to be considered as labile with respect to their redox properties.

We have now found conditions which permit the preparation of the desired product XIV in good yields, without the formation of more highly brominated by-products. According to the reaction conditions of the invention, the preferred reagent is tetrabutylammonium tribromide. The solvents used are haloalkanes, such as 1,2-dichloroethane or methylene chloride, alcohols, such as methanol, ethanol, n-propanol, isopropanol, aliphatic nitriles, such as acetonitrile, preferably acetonitrile. The preferred base is potassium carbonate. The brominated intermediates XIV can then be converted by various routes into the isoxazol-3-ylbromobenzenes X according to the invention. The steps for preparing compounds IX from XIV or compounds X from IX can be prepared by the processes already mentioned above.

However, alternatively, it is also possible to initially convert the anilines into the sulfonyl chlorides X.c (see Houben-Weyl, Vol. IX, p. 579–580). These can be converted into the alkyl sulfones by reduction of the sulfonyl chlorides, for example using sodium sulfite, via the stage of the sulfinic acids (see Houben-Weyl, Vol. IX, p. 306–307) and subsequent alkylation (see Houben-Weyl, Vol. IX, p. 231–233).

The two steps can advantageously be combined in a "one-pot reaction". The advantage of this synthesis is the use of favorable reagents for introducing the alkylsulfonyl groups.

The step of the oximation of substituted toluenes used in process step a) of the process according to the invention is a novel and advantageous process for converting toluene derivatives into benzaldoximes. In principle, this process is suitable for producing benzaldoximes of the formula XV

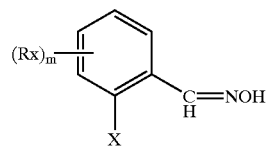

XV in which the radicals are as defined below:
X is $NO_2$, $S(O)_nRy$,
Rx is any inert radical;
Ry is any inert radical;
m is 0, 1, 2, 3 or 4,
n is 0, 1 or 2.

Rx, Ry are any organic radicals, which can be identical or different and which are chemically inert under the chosen reaction conditions. Examples which may be mentioned for Rx are: halogen, such as, for example, chlorine, bromine or iodine; carboxyl; carboxamide; N-alkylcarboxamides and N,N-dialkyl-carboxamides; phenyl; $C_1$–$C_6$-alkyl, such as, for example, methyl, ethyl; $C_1$–$C_6$-alkoxy; $C_1$–$C_6$-alkylthio or other radicals. If m>1, Rx can in each case be identical or different. Rx preferably has the same meaning as $R^1$ and is located ortho to the oxime group —CH=NOH. m is in particular the number 2, one of the substituents Rx having the same meaning as $R^1$ and the other substituent Rx being a halogen atom, which is preferably located in the position meta to the oxime group. Ry is preferably $C_1$–$C_6$-alkyl, for example methyl, ethyl, propyl.

Preferred compounds XV are those in which X denotes the group $SO_2$-Ry and m is the number 2. In this case, one of the radicals Rx is preferably halogen (for example bromine or chlorine) and is located in the position meta to the oxime group. The second radical Rx is preferably $C_1$–$C_6$-alkyl (for example methyl, ethyl) and is located in the position ortho to the oxime group.

According to the invention, compounds of the formula XVI (o-nitrotoluene or o-alkylsulfonyltoluene)

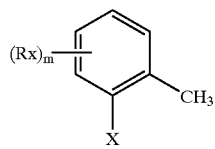

XVI in which the substituents are each as defined above, are reacted with an organic nitrite of the formula R—O—NO, as already defined, under action of a base.

The nitrosation of o-nitrotoluene has been described in the literature (Lapworth, J. Chem. Soc. 79 (1901), 1265). However, even in this early work, a dimeric by-product is mentioned. Later works only describe the preparation of dimeric products under similar reaction conditions (Das et al., J. Med. Chem. 13 (1970), 979). A repetition of the experiment described in the literature with o-nitrotoluene shows that small amounts of 2-nitrobenzaldoxime are indeed formed.

If the conditions described are applied to 3-nitro-o-xylene, the dimer XVIII is obtained exclusively.

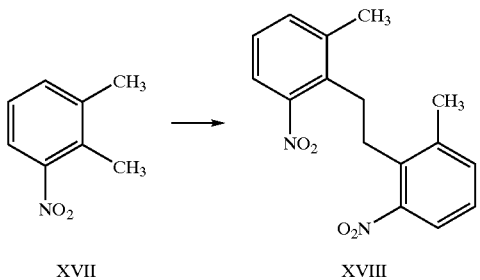

XVII                XVIII

For Michael additions proceeding under similar conditions, too, there is a note in the literature that they do not succeed with 3-nitro-o-xylene (Li, Thottathil, Murphy, Tetrahedron Lett. 36 (1994), 6591). According to the prior descriptions, it is therefore unexpected that benzaldoximes can be prepared from 6-substituted 2-nitrotoluenes in excellent yields. Moreover, we have surprisingly found that alkylsulfonates (X=SO$_2$Ry) can also be oximated under similar conditions at the methyl group in the o position. The compounds prepared by the process of the invention are important intermediates for preparing active compounds for crop protection agents (WO 98/31681).

The reaction is preferably carried out under the following conditions: the solvents used are: dipolar aprotic solvents, for example N,N-dialkylformamides, N,N-dialkylacetamides, N-methylpyrrolidone, preferably: DMF, NMP. The temperature is from –60° C. to room temperature; preferably from –50 to –20° C.; particularly preferably –35 to –25° C. To achieve a sufficiently low melting point of the solvent system, it is also possible to use mixtures of solvents, such as, for example, with THF. Preferred nitrites or alkyl nitrites are n-butyl nitrite and (iso)amyl nitrite. Suitable bases are: (M=alkali metal): Moalkyl, MOH, RMgX; preferably KOMe, NaOMe, potassium t-butoxide. When using sodium bases, preference is given to adding 1–10 mol % of amyl alcohol. The stoichiometry is as follows: 1–4 equivalents of base, 1–2 equivalents of R—ONO; preferably: 1.5–2.5 equ. of base, 1–1.3 equ. of RONO (i.e. an organic nitrite), equally preferably 1–2 equivalents of base and 1–1.3 equivalents of R—ONO. The order of the metered addition: a) compound of the formula XVI and nitrite are initially charged and the base is metered in. b) To avoid metered addition of the solid base, the base can be initially charged in DMF, and compound of the formula XVI/nitrite can be added simultaneously. It is advantageous to meter in the base over a prolonged period to reduce the cooling that is required.

Work-up is carried out, for example, as follows: a) precipitation by stirring the mixture into water/acid e.g. water/hydrochloric acid. b) Precipitation by addition of a sufficient amount of water/acid. Suitable acids are mineral acids, such as sulfuric acid, hydrochloric acid or phosphoric acid, or else carboxylic acids, such as acetic acid. Purification of the product: by extraction with toluene at from 0 to 110° C., preferably at room temperature.

If the reaction is carried out at elevated temperature (from –10 to 0° C.) and the mixture is subsequently stirred at room temperature, work-up gives the benzonitriles directly. It is furthermore possible to liberate the aldehyde function from the benzaldoximes of the formula XV in the presence of an acidic catalyst and an aliphatic aldehyde e.g. aqueous formaldehyde solution. Suitable solvents are haloalkanes, such as 1,2-dichloroethane or methylene chloride, aromatics, such as benzene, toluene, chlorobenzene, nitrobenzene or xylene, polar aprotic solvents, for example N,N-dialkylformamides, -acetamides, N-methylpyrrolidone, dimethylpropylene urea; tetramethyl urea, tetrahydrofuran, acetonitrile, propionitrile or acetone, with or without addition of water. Particularly advantageous is aqueous acetone (from 1 to 20% of water), dioxane/water mixtures, and tetrahydrofuran/water mixtures. The reaction is carried out at from room temperature to the reflux temperature of the solvent, preferably at from 30 to 70° C. Suitable acids are mineral acids, such as aqueous hydrochloric acid, sulfuric acid or phosphoric acid, acidic ion exchangers, such as Amberlyst 15 or Dowex 50 W×8.

In the case of the compounds of the formula XV, it is then possible to convert the oxime group —CH=NOH into the corresponding aldehydes (—CHO) or else into the corresponding nitrites (—CN). These compounds are important synthesis building blocks for preparing active compounds of the formula I (cf. WO 98/31681).

The thioalkylation step used in process step d) of the process according to the invention is a novel and advantageous process for converting aniline derivatives into thioether derivatives (thioalkylation of aniline derivatives). In principle, the process is generally suitable for preparing thioethers of the formula XIX

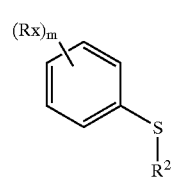

XIX where Rx is any inert radical, m is a number 0–5 and $R^2$ is a $C_1$–$C_6$-alkyl group, which comprises reacting an aniline of the formula XX

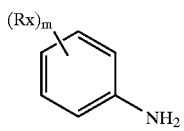
                              XX with a dialkyl disulfide of the formula VII

                                VII in the presence of a catalyst. Preferred catalysts are copper powder, in particular copper powder having a particle size of less than 70 μm, or elemental copper in another form, such as, for example, turnings, wire, granules, shot or rods. It is also possible to use copper(I) salts, for example copper(I) chloride, copper(I) bromide or copper(I) iodide, copper(II) salts, or elemental iodine. Particular preference is given to using copper powder.

In the compounds of the formulae XIX and XX, Rx is any radical which is chemically inert under the chosen reaction conditions during the reaction with compounds of the formula VII. Thus, suitable groups Rx are, for example, the following groups: hydrogen, alkyl, haloalkyl, halogen, cyano, nitro, alkoxy, haloalkoxy, alkylthio or heterocyclic radicals as mentioned at the outset in the definition of $R^6$. Suitable heterocyclic radicals are, in particular, unsubstituted or alkyl-substituted 5-membered heterocyclic saturated, partially saturated or aromatic rings from the group consisting of isoxazolines, isoxazoles, thiazolines, thiazoles, oxazoles and pyrazoles. The compounds of the formulae XIX and XX can carry one or more, preferably one, two or three, substituents Rx, which can be identical or different.

Rx is preferably a $C_1$–$C_6$-alkyl group, for example methyl, ethyl, propyl. m is preferably the number 1 or 2. If m is the number 1, Rx is preferably located ortho or meta to the group —S—$R^2$ (in the case of the compounds XIX) or to the amino group (in the case of the compounds XX). If m is the number 2, the second radical Rx is preferably located in the position ortho and meta to the group —S—$R^2$ or the amino group.

Thioethers of the formula XIX are useful intermediates for preparing active compounds in the chemical industry, for example for preparing crop protection agents (e.g. WO 96/11906; WO 98/31676) or for preparing drugs. A process for introducing alkylthio functions which is frequently used is the exchange of a halogen (EP 0 711 754). However, the process described therein has the disadvantage that it is limited to aromatics which are substituted by strongly electron-withdrawing radicals. Moreover, the preparation frequently requires high temperatures. Under these reaction conditions, other sensitive functional groups are chemically modified, giving rise to complex reaction mixtures whose purification is complicated and associated with high cost, and in certain cases it is no longer possible to remove the impurities at all. In addition, suitable precursors are also not always commercially available.

Methods for preparing arylalkyl sulfides from anilines are known, but these methods have serious disadvantages. The Sandmeyer reaction, for example, requires the use of equimolar amounts of copper alkylthiolate (Baleja, Synth. Commun. 14 (1984), 215–218). The yields obtained are typically only in the range of from 20 to 60%.

Another method that has been described is the reaction of aromatic amines with alkyl nitrites in excess dialkyl sulfide (Giam et al., J. Chem. Soc., Chem. Commun. 1980, 756–757). Here, there is the problem that, in some cases to a considerable extent, side reactions occur which result in poor yields and high expenses for product purification. Moreover, when the reaction was carried out in an inert diluent, it was observed that, after an induction phase, a very violent reaction which was difficult to control set in, thus excluding industrial use.

It is an object of the present invention to provide an alternative preparation process for thioethers.

We have found that this object is achieved by the preparation process according to the invention, which permits the preparation of aromatic alkyl thioethers from anilines in an advantageous manner. Using the process, it is possible to carry out the preparation in a simple, cost-effective and efficient manner, taking into account ecological and economically advantageous aspects.

According to the invention, the aniline is reacted with a dialkyl disulfide and an organic nitrite R—ONO following the reaction scheme shown above in the presence of a catalyst, preferably of elemental copper. Comparative experiments show that, using the conditions according to the invention, considerably better yields are obtained and less by-products are formed than without a catalyst. Moreover, the reaction is easy to control and can be employed industrially.

The reaction is carried out using the reaction conditions described in more detail below: suitable solvents are haloalkanes, such as 1,2-dichloroethane or methylene chloride, aromatics, such as benzene, toluene, chlorobenzene, nitrobenzene. Alternatively, it is also possible to employ an excess of the dialkyl disulfide itself as solvent. This variant is particularly advantageous. The reaction is carried out at from 40° C. to 150° C., preferably from 60 to 100° C. and in particular from 70 to 90° C. It may also be advantageous to carry out the reaction in a temperature range of 45–70° C., in particular in a range of 55–65° C. In the reaction, it is advantageous to add a $C_1$–$C_6$-alkyl nitrite reagent. In this respect, suitable reagents are, for example, n-butyl nitrite, (iso)amyl nitrite or tert-butyl nitrite. The stoichiometry is in this case, for example, 1–3 equivalents of alkyl nitrite, preferably 1–1.5 equivalents of alkyl nitrite, particularly preferably 1–1.3 equivalents of alkyl nitrile. Suitable catalysts are copper powder or elemental copper in another form, copper(I) salts, for example copper(I) chloride, copper(I) bromide or copper(I)iodide, copper(II) salts, or elemental iodine, preferably copper powder or elemental copper in another form; copper salts are equally preferable. The reaction is carried out, for example, using the following stoichiometric ratios: if the reaction is carried out in a solvent: 1–3 equivalents of dialkyl disulfide, preferably 1–2 equivalents. If the reaction is carried out without an additional solvent, i.e. if the dialkyl disulfide is used as solvent: use of an excess of dialkyl disulfide or mixtures of dialkyl disulfides, which can subsequently be recovered by distillation. The product is purified, for example, by distillation or crystallization (for example from diisopropyl ether).

The present invention furthermore provides a process for preparing compounds X using the above-described process for the oximation of substituted toluenes XVI (cf. process step a)) and/or using the above-described process for the thioalkylation of aniline derivatives XX (cf. process step d)). In the reaction scheme 4 below, a suitable preparation process is described using the example of a compound X where $R^1$=$CH_3$, $R^2$=$CH_3$, $R^3$=$R^4$=$R^5$=H. In principle, the process is also suitable for preparing compounds X where the radicals $R^1$–$R^5$ are as defined above.

Scheme 4:

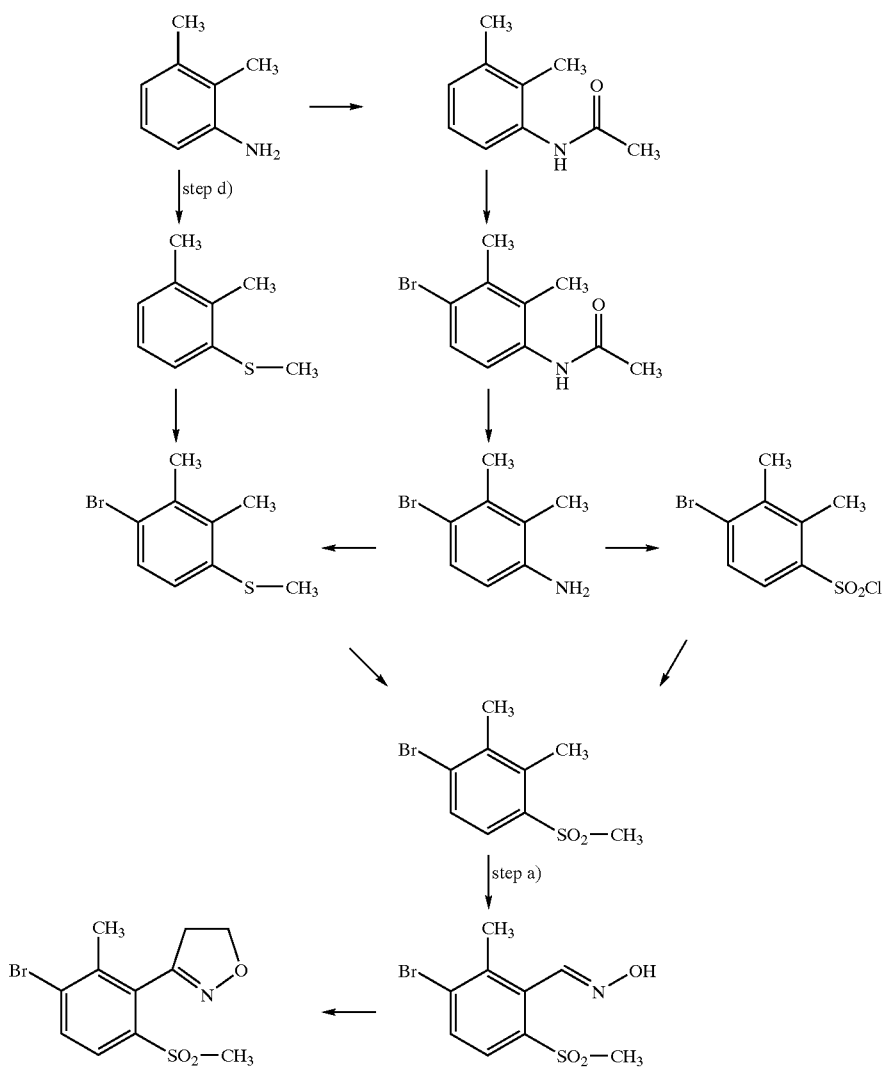

The invention is illustrated in more detail in the working examples below. Examples 1–9 relate to process steps a)–g). Examples 10–26 relate to the preparation of starting materials or intermediates or to corresponding comparative examples. Example 27 relates to the reaction sequence for preparing compounds X shown in scheme 4.

EXAMPLE 1

Preparation of 2-methyl-6-nitrobenzaldoxime (process step a)—variant A)

A solution of 274 g (2.6 mol) of n-butyl nitrite (97% pure) and 300 g (2.0 mol) of 3-nitro-o-xylene (97% pure) in 750 ml of dimethylformamide is cooled to from −55 to −60° C., and a solution of 522 g (4.56 mol) of potassium tert-butoxide in 750 ml of dimethylformamide is added dropwise at this temperature, over a period of 2.5 hours. The color of the solution changes from yellow to deep red, and the consistency becomes viscous. The reaction is monitored by HPLC. For work-up, initially 300 ml of water are added, and subsequently approximately 300 ml of glacial acetic acid, until the pH is 5–6. During the addition, the temperature rises to −10° C., and a yellow suspension is formed. The reaction mixture is subsequently poured into 6 kg of ice-water, and the residue that has formed is filtered off with suction, washed with 5 l of water and dried in a drying cabinet at 30° C. overnight.

This gives 339 g of a light-beige crude product which is freed from impurities by suspending it in approximately 3 l of toluene at 80–90° C. for 2 hours. After cooling, the product is filtered off with suction and dried. This gives 276 g of 2-nitro-6-methylbenzaldoxime.

Yield: 77%, m.p.: 190–192° C., purity (according to HPLC): 98%.

EXAMPLE 2

Preparation of 2-methyl-6-nitrobenzaldoxime (process step a)—variant B)

1200 ml of anhydrous DMF are initially charged in a 4 l reaction flask and cooled to −40° C. At this temperature, 336.5 g (4.56 mol) of potassium methoxide (95%) are added with stirring and suspended. A mixture of 300 g (1.92 mol) of 3-nitro-o-xylene (97%) and 274 g (2.52 mol) of n-butyl nitrite (95%) is subsequently added dropwise at −40° C. over a period of 7 hours (if the mixture is cooled appropriately, the duration of this addition can be reduced at will; an extension has hitherto not been examined; temperature variations between −35 and −45° C. can be tolerated). By HPLC, it is checked that the starting material has been converted completely. The reaction discharge is subsequently added with stirring to a mixture of 300 ml of water and 300 ml of glacial acetic acid, at from −5 to 0° C. The reaction mixture is then poured into 6 kg of ice-water and the solid is separated off by filtration (without any problems, the flow resistance has not yet been determined) and washed twice with 500 ml of water each time (caution: the crude product smells strongly). The crude product (HPLC: 96 area %) is purified by suspending the moist solid in 800 ml of toluene for 1.5 h. The solid is filtered off (without any problems, the flow resistance has not yet been determined) and dried in a vacuum drying cabinet at 50° C.

Yield: 306 g (HPLC: 99.4 area % of product; E/Z mixture), corresponding to 85% of theory.

EXAMPLE 3

Preparation of 3-(2-methyl-6-nitrophenyl)-4,5-dihydroisoxazole (process step b))

a) At 60° C., a small amount of a solution of 3.71 g (28 mmol) of N-chlorosuccinimide in 30 ml of acetonitrile is added to a solution of 5 g (28 mmol) of 2-methyl-6-nitrobenzaldoxime in 50 ml of acetonitrile. After the reaction has started, the remaining solution is slowly added dropwise at 40–50° C. The reaction mixture is stirred for another 20 minutes until the reaction has, according to HPLC, gone to completion. An orange solution results, which is carefully concentrated. The residue is suspended in 50 ml of toluene for approximately 1.5 hours, and the solution is separated off from the succinimide. The filtrate is still orange-red. The solution is filled into a mini autoclave, and an ethylene pressure of 30 bar is applied. Over a period of 5 hours, a solution of 4.7 g of sodium bicarbonate in 50 ml of water is then metered in, and the mixture is stirred at an ethylene pressure of 30 bar for another 5 hours. For work-up, the phases are separated and the toluene phase is washed 2×with NaHCO$_3$ solution and 1×with water, dried and concentrated. Yield: 4.9 g (86%) of brownish crystals, m.p.: 100–105° C.

1H-NMR (CDCl$_3$): δ=8.00 (d, 1H); 7.57 (d, 1H); 7.49 (t, 1H); 4.60 (t, 2H); 3.32 (t, 2H); 2.41 (s, 3H).

b) 100 g of 2-methyl-6-nitrobenzaldoxime are dissolved in 750 ml of glacial acetic acid, and chlorine is then introduced for 2 hours. Excess chlorine is flushed out with nitrogen. The glacial acetic acid is subsequently distilled off, and the residue is suspended in 1000 ml of toluene. The reaction mixture is filled into the autoclave, and an ethylene pressure of 6 bar is applied. Over a period of 1 hour, 55.6 g of triethylamine (1 equ.) in 300 ml of toluene are metered in, and the mixture is stirred at room temperature and an ethylene pressure of 6 bar for 10 h. The reaction mixture is washed once with saturated aqueous NaHCO$_3$ solution and once with water. The organic phase is dried over sodium sulfate and filtered off, and the filtrate is concentrated. Yield: 96.3 g (87% of theory).

EXAMPLE 4

Preparation of 2-(4,5-dihydroisoxazol-3-yl)-3-methylaniline (process step c))

a) A hydrogenation autoclave is filled with a solution of 117 g (0.57 mol) of 3-(2-methyl-6-nitrophenyl)-4,5-dihydroisoxazole in 1.2 l of ethyl acetate and 11.7 g of a catalyst containing 5% by weight of platinum on carbon. The autoclave is then flushed twice with nitrogen. Hydrogenation is subsequently carried out at 25–30° C. and a hydrogen pressure of 20 bar with intensive stirring for 48 hours. The reaction discharge is filtered off with suction through silica gel, and the solvent is stripped off under reduced pressure. This gives 94 g of a brown solid which is taken up in methyl tert-butyl ether and water and extracted with 1 M hydrochloric acid. The aqueous phase is adjusted to pH 10–11 and extracted with methylene chloride. The methylene chloride phase is dried over magnesium sulfate, and the solvent is stripped off.

Yield 87 g (87%) of an orange solid, m.p.: 86–88° C., purity according to HPLC 97%.

The product can be purified further by stirring with methyl tert-butyl ether under reflux: m.p.: 90–91° C., purity according to HPLC 100% b) A solution of 1 000 g (4.85 mol) of 3-(2-methyl-6-nitro-phenyl)-4,5-dihydroisoxazole in 5.5 ml of methanol and 4.6 g of a catalyst containing 10% by weight of Pd on carbon is added to a hydrogenation autoclave. The autoclave is then flushed twice with nitrogen. The mixture is then hydrogenated at 25–30° C. and under a hydrogen pressure of 2.5 bar with vigorous stirring for 17 hours. The reaction discharge is filtered off with suction through silica gel, and the solvent is distilled off under reduced pressure.

This gives 781.7 g of a light-brown solid.

Yield 781.7 g (85%) (content according to HPLC 93%).

EXAMPLE 5

Preparation of 3-(2-methyl-6-methylthiophenyl)-4,5-dihydroisoxazole (process step d)—variant A)

19.5 g (170 mmol) of tert-butylnitrite and 20 g of copper powder are initially charged in 30 ml of dimethyl disulfide, and a solution of 20 g (114 mmol) of 2-(4,5-dihydroisoxazol-3-yl)-3-methylaniline in 100 ml of dimethyl disulfide is added dropwise at from 50 to 55° C. The mixture is subsequently stirred at 60° C. for 1.5 hours. For work-up, the solid is filtered off with suction, and the filtrate is diluted with methylene chloride and extracted with dilute hydrochloric acid. The organic phase is washed with saturated aqueous NaHCO$_3$ solution and dried over sodium sulfate, the drying agent is filtered off and the filtrate is concentrated. Excess dimethyl disulfide is removed under oil pump vacuum.

This gives 23.4 g (99%) of a dark oil which solidifies after some time. (Content according to HPLC 100%). The product can be purified further by stirring in methyl tert-butylether. M.p.: 66–67° C.

Preparation of 3-(2-methyl-6-methylthiophenyl)-4,5-dihydro-isoxazole (process step d)—variant B)

40 g (0.22 mol) of 2-(4,5-dihydroisoxazol-3-yl)-3-methylaniline and 1.5 g of copper powder are initially charged in 300 ml of dimethyl disulfide, and 26.1 g of n-butyl nitrite (0.23 mol) are added dropwise at 55–66° C. The mixture is then stirred at 60° C. for 1.5 hours. For work-up, the hot mixture is filtered through activated carbon and then washed with dilute hydrochloric acid and water and then concentrated under reduced pressure. This gives 44.5 g (88%) of a dark oil which solidifies after a while (content according to HPLC (95%). The product can be purified further by trituration with methyl tert-butyl ether.

Preparation of 3-(2-methyl-6-methylthiophenyl)-4,
5-dihydroisoxazole (process step d)—variant C)

25 g (0.14 mol) of 2-(4,5-dihydroisoxazol-3-yl)-3-methylaniline and 0.2 g of copper(II) chloride are initially charged in 200 ml of dimethyl sulfide, and 16.1 g of n-butyl nitrite (0.15 mol) are added dropwise at 55–62° C. The mixture is then stirred at 60° C. for 0.5 hours. For work-up, the mixture is then washed with dilute hydrochloric acid and water and then concentrated under reduced pressure. This gives 26.3 g (91%) of a dark oil which solidifies after a while (content according to HPLC 96%). The product can be purified further by trituration with methyl tert-butyl ether.

Preparation of 3-(2-methyl-6-methylthiophenyl)-4,
5-dihydroisoxazole (process step d)—variant D)

40 g (0.22 mol) of 2-(4,5-dihydroisoxazol-3-yl)-3-methylaniline and 0.44 g of copper(I) chloride are initially charged in 300 ml of dimethyl sulfide, and 26.1 g of n-butyl nitrite (0.23 mol) are added dropwise at 55–66° C. The mixture is then stirred at 60° C. for 1.5 hours. For work-up, the mixture is then washed with dilute hydrochloric acid and water and then concentrated under reduced pressure. This gives 38.7 g (85%) of a dark oil which solidifies after a while (content according to HPLC 94%). The product can be purified further by trituration in methyl tert-butyl ether.

EXAMPLE 6

Preparation of 3-(3-bromo-2-methyl-6-methylthiophenyl)-4,5-dihydroisoxazole (process step e))

At 0° C., 10 g (48 mmol) of 3-(2-methyl-6-methylthiophenyl)-4,5-dihydroisoxazole are added a little at a time to 120 ml of conc. sulfuric acid, and the mixture is stirred for approximately 30 minutes. 3.7 g (23 mmol) of bromine are then added dropwise, and the mixture is stirred at 0° C. for 2.5 hours. Over a period of approximately 45 minutes, the mixture is subsequently allowed to warm to room temperature. A homogeneous solution forms. For work-up, the reaction mixture is poured into ice-water and extracted three times with methylene chloride. The organic phase is washed with sodium bicarbonate solution, dried with magnesium sulfate and concentrated. This gives 11.4 g of crude product which is employed in the next step without any further purification.

EXAMPLE 7

Preparation of 3-(3-bromo-2-methyl-6-methylsulfonylphenyl)-4,5-dihydroisoxazole
(process step f))

At at most 45° C., 11.3 g (100 mmol) of 30% strength hydrogen peroxide are added dropwise to a solution of 11.4 g (40 mmol) of 3-(3-bromo-2-methyl-6-methylthiophenyl)-4,5-dihydroisoxazole and 400 mg of sodium tungstate hydrate in 100 ml of glacial acetic acid. The reaction mixture is stirred at room temperature overnight. For work-up, the mixture is poured into ice-water and extracted with methylene chloride, and the organic phase is washed with aqueous sodium sulfite solution, dried over magnesium sulfate and concentrated. Yield: 9.6 g. For purification, the product can be recrystallized from 65 ml of isopropanol.

Yield: 7.7 g (50% over 2 steps), m.p. 137–139° C.

EXAMPLE 8

1-Methyl-4-(3-(4,5-dihydroisoxazol-3-yl)-2-methyl-4-methylsulfonylbenzoyl)-5-hydroxypyrazole
(process step g)—variant A)

2.2 l of 1,4-dioxane, 100 g (0.315 mol) of 3-(3-bromo-2-methyl-6-methylsulfonylphenyl)-4,5-dihydroisoxazole, 30.82 g (0.315 mol) of 1-methyl-5-hydroxypyrazole, 87 g (0.63 mol) of potassium carbonate, 63.5 g (0.63 mol) of triethylamine and 11.2 g (0.016 mol) of bis(triphenylphosphine)-palladium dichloride were added to a 3.5 l autoclave. The autoclave was then flushed twice with nitrogen, a carbon monoxide pressure of 10 kg/cm$^2$ was applied and the mixture was heated with stirring to 130° C. The carbon monoxide pressure was increased to 20 kg/cm$^2$ and the mixture was stirred at 130° C. for 24 h. The mixture was then concentrated under reduced pressure and the residue was taken up in water. The aqueous phase of pH 11 was extracted with dichloromethane. The organic phase is discarded. The aqueous phase is adjusted to pH 4 using 18% strength hydrochloric acid. The precipitate was filtered off, washed three times with water and dried at 40° C. under reduced pressure. This gives 85 g of product. The filtrate is extracted with dichloromethane. The organic phase is dried with sodium sulfate, and the solvent is then removed under reduced pressure, giving a further 12.7 g of product.

Yield 97.7 g (85.6%), m.p.: 215–219° C., $^1$H-NMR (CDCl$_3$): δ=2.38 (s); 3.23 (s); 3.41 (bs); 3.74 (s); 4.61 (t); 7.37 (s); 7.64 (d); 8.16 (d).

EXAMPLE 9

1-Methyl-4-(3-(4,5-dihydroisoxazol-3-yl)-2-methyl-4-methyl-sulfonylbenzoyl)-5-hydroxypyrazole
(process step g)—variant B)

2 l of 1,4-dioxane, 250 g (0.77 mol) of 3-(3-bromo-2-methyl-6-methylsulfonylphenyl)-4,5-dihydroisoxazole, 77 g (0.77 mol) of 1-methyl-5-hydroxypyrazole, 269 g (1.93 mol) of potassium carbonate, 197 g (1.93 mol) of triethylamine, 1.39 g (0.0077 mol) of palladium(II) chloride and 4.12 g (0.0154 mol) of triphenylphosphine were added to a 3.5 l autoclave. The autoclave was washed twice with nitrogen, the mixture was heated with stirring to 130° C. and a carbon monoxide pressure of 6 kg/cm$^2$ was applied. By continuous addition of carbon monoxide, the carbon monoxide pressure was kept constant at 6 kg/cm$^2$ and the mixture was stirred at 130° C. for 36 h. The mixture was then admixed with 1 l of demineralized water and the precipitated palladium was filtered off over a blue-band filter (pore size 2 to 3 μ) and washed with water. Dioxane, triethylamine and some of the water were then distilled off in one step (150 mbar or atmospheric pressure). The aqueous phase was adjusted to pH 2.5 using 20% strength sulfuric acid and stirred at 5° C. for 12 h, while the pH was being readjusted. The precipitate was filtered off, washed three times with water and dried at 70° C. under reduced pressure. This gave 227 g of product (calc. 100%).

Yield 227 g (81%), m.p.: 215–219° C., $^1$H-NMR (CDCl$_3$): δ=2.38 (s); 3.23 (s); 3.41 (bs); 3.74 (s); 4.61 (t); 7.37 (s); 7.64 (d); 8.16 (d).

Palladium recovery rate on filter: 85–98%

Elemental analysis of the palladium that was filtered off (dried): Pd 48%, O 22%, C 11%, H 1.3%, P 0.2%, S 0.2%, Br<0.5%, Cl<0.5%, N<0.5%.

EXAMPLE 10

Preparation of 4-bromo-2-(4,5-dihydroisoxazol-3-yl)-3-methylaniline 30 g (170 mmol) of 2-(4,5-dihydroisoxazol-3-yl)-3-methylaniline are dissolved in 400 ml of acetonitrile, and 94 g (0.68 mol) of potassium carbonate are added. 84 g (174 mmol) of tetrabutylammonium tribromide are subsequently added a little at a time with vigorous stirring at temperatures<30° C. For work-up, the solid is filtered off with suction and the filtrate is diluted with methylene chloride and extracted with water. The solvent is stripped off and the residue is again taken up in methyl tert-butyl ether and washed twice with water. The organic phase is dried and concentrated.

Yield 20.4 g (47%) of a brown solid, m.p.: 126–130° C., purity according to HPLC 97%

EXAMPLE 11

Preparation of 4-bromo-2-(4,5-dihydroisoxazol-3-yl)-3-methylbenzenesulfonyl chloride At 15° C., a solution of 9 g (35 mmol) of 4-bromo-2-(4,5-dihydroisoxazol-3-yl)-3-methylaniline in 50 ml of glacial acetic acid is added to 15 ml of conc. hydrochloric acid. At 5–10° C., a solution of 2.44 g (35 mmol) of sodium nitrite in 10 ml of water is then added dropwise, and the mixture is stirred at 5° C. for 1 hour. At room temperature, this solution is then added dropwise to a mixture of a solution of 47 g (0.74 mol) of sulfur dioxide in 100 ml of glacial acetic acid and a solution of 2.23 g (13 mmol) of copper(II) chloride in 5 ml of water. The reaction mixture is stirred at room temperature for 1 hour and subsequently poured into 300 ml of ice-water and extracted with methylene chloride. The organic phase is washed with water, dried with magnesium sulfate and concentrated.

Yield 11.8 g (99%), purity according to HPLC 96%

In the working examples below, the preparation of benzaldoximes of the formula XV (process step a) is described in more detail:

EXAMPLE 12

Preparation of 2-methyl-6-nitrobenzaldoxime
(variant A)

A solution of 274 g (2.6 mol) of n-butyl nitrite (97% pure) and 300 g (2.0 mol) of 3-nitro-o-xylene (97% pure) in 750 ml of dimethylformamide is cooled to from −55 to −60° C., and a solution of 522 g (4.56 mol) of potassium tert-butoxide in 750 ml of dimethylformamide is added dropwise at this temperature, over a period of 2.5 hours. The color of the solution changes from yellow to deep red, and the consistency becomes viscous. The reaction is monitored by HPLC. For work-up, initially 300 ml of water are added, and subsequently approximately 300 ml of glacial acetic acid, until the pH is 5–6. During the addition, the temperature rises to −10° C., and a yellow suspension is formed. The reaction mixture is subsequently poured into 6 kg of ice-water, and the residue that has formed is filtered off with suction, washed with 5 l of water and dried in a drying cabinet at 30° C. overnight. This gives 339 g of a light-beige crude product which is freed from impurities by suspending it in approximately 3 l of toluene at 80–90° C. for 2 hours. After cooling, the product is filtered off with suction and dried. This gives 276 g of 2-nitro-6-methylbenzaldoxime.

Yield: 77%, m.p.: 190–192° C., purity (according to HPLC): 98%

EXAMPLE 13

Preparation of 2-methyl-6-nitrobenzaldoxime
(variant B)

1200 ml of anhydrous DMF are initially charged in a 4 l reaction flask and cooled to −40° C. At this temperature, 336.5 g (4.56 mol) of potassium methoxide (95%) are added with stirring and suspended. A mixture of 300 g (1.92 mol) of 3-nitro-o-xylene (97%) and 274 g (2.52 mol) of n-butyl nitrite (95%) is subsequently added dropwise at −40° C. over a period of 7 hours (if the mixture is cooled appropriately, the duration of this addition can be reduced at will). By HPLC, it is checked that the starting material has been converted completely. The reaction discharge is subsequently added with stirring to a mixture of 300 ml of water and 300 ml of glacial acetic acid, at from −5 to 0° C. The reaction mixture is then poured into 6 kg of ice-water and the solid is separated off by filtration and washed twice with 500 ml of-water each time.

The crude product (HPLC: 96 area %) is purified by suspending the moist solid in 800 ml of toluene for 1.5 h. The solid is filtered off and dried in a vacuum drying cabinet at 50° C.

Yield: 306 g (HPLC: 99.4 area % of product; E/Z mixture), corresponding to 85% of theory.

EXAMPLE 14

Preparation of 2-chloro-6-nitrobenzaldoxime

A solution of 4.1 g (40 mmol) of n-butyl nitrite (97% pure) and 5 g (29 mmol) of 2-chloro-6-nitrotoluene in 50 ml of dimethylformamide is cooled to from −55 to −60° C., and a solution of 3.3 g (29.5 mmol) of potassium tert-butoxide in 30 ml of dimethylformamide is added dropwise at this temperature, over a period of 20 minutes. The reaction is monitored by HPLC. For work-up, initially water is added, and the pH is subsequently adjusted to 5–6 using glacial acetic acid. The product is isolated by extraction with ethyl acetate. This gives 5.7 g of 2-chloro-6-nitrobenzaldoxime.
$^1$H NMR (CDCl$_3$): δ=8.00 (d, 1H); 7.84 (s, 1H); 7.76 (d, 1H); 7.52 (t, 1H).

EXAMPLE 15

Preparation of 3-chloro-2-methyl-6-methylsulfonylbenzaldoxime

A solution of 12.7 g (119 mmol) of n-butyl nitrite (97% pure) and 20 g (92 mmol) of 2,3-dimethyl-4-methylsulfonylchlorobenzene in 100 ml of dimethylformamide is cooled to from −55 to −60° C., and a solution of 16.8 g (147 mmol) of potassium tert-butoxide in 70 ml of dimethylformamide is added dropwise at this temperature, over a period of 30 minutes. The reaction is monitored by HPLC. For work-up, initially 50 ml of water are added, and the pH is subsequently adjusted to 5–6 using approximately 30 ml of glacial acetic acid. The reaction mixture is subsequently poured into 0.7 kg of ice-water, and the aqueous phase is extracted with methylene chloride. The organic phase is washed with sodium bicarbonate solution, dried over magnesium sulfate and concentrated. This gives 18.4 g of a light-beige crude product which is purified by recrystallization from approximately 30 ml of toluene.

Yield: 6.15 g (27%) of white crystals, m.p.: 164–168° C., purity (according to HPLC): 100%

EXAMPLE 16

Preparation of 3-bromo-2-methyl-6-methylsulfonylbenzaldoxime

A solution of 2.1 g (20 mmol) of n-butyl nitrite (97%) pure and 4 g (15 mmol) of 2,3-dimethyl-4-methylsulfonylbromobenzene in 50 ml of dimethylformamide is cooled to from −55 to −60° C., and a solution of 2.8 g (25 mmol) of potassium tert-butoxide in 35 ml of dimethylformamide is added dropwise at this temperature, over a period of 20 minutes. The reaction is monitored by HPLC. For work-up, initially 10 ml of water are added, and the pH is subsequently adjusted to 5–6 using approximately 9 ml of glacial acetic acid. The reaction mixture is subsequently poured into 100 ml of ice-water, and the aqueous phase is extracted with methylene chloride. The organic phase is washed with sodium bicarbonate solution, dried over magnesium sulfate and concentrated. This gives 3.6 g of an oily crude product (90% pure according to HPLC) which can be purified by recrystallization from toluene.

Yield: 1.22 g (27%), m.p.: 192–194° C., purity (according to HPLC): 99%

EXAMPLE 17

Preparation of N,N-diphenyl-3-hydroxyimino-2-methyl-4-methylsulfonylbenzamide a) Preparation of the Precursor

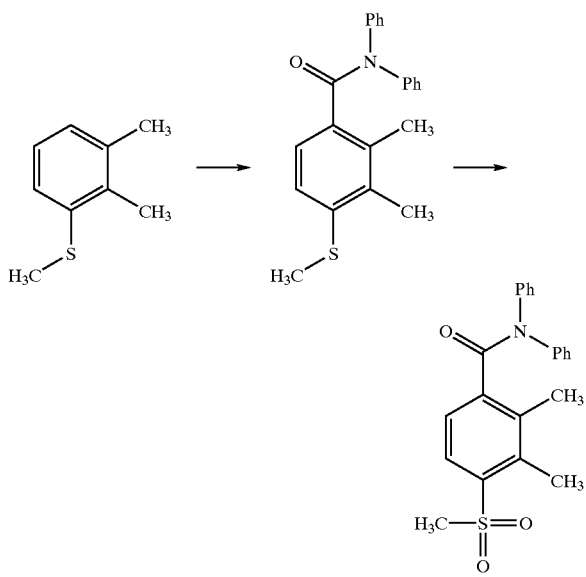

5 g (3 mmol) of 2,3-dimethylthioanisole and 7.6 g (33 mmol) of diphenylcarbamoyl chloride are dissolved in 50 ml of 1,2-dichloroethane and, at room temperature, admixed with 4.8 g (36 mmol) of anhydrous aluminum chloride. The reaction mixture is boiled at reflux for 3 hours, poured into a mixture of ice and concentrated hydrochloric acid, and the aqueous phase is extracted twice with methylene chloride. The organic phase is washed with sodium bicarbonate solution, dried over magnesium sulfate and concentrated. This gives 10.8 g of crude product which is purified by silica gel chromatography using toluene/ethyl acetate as mobile phase. Yield 7.8 g of N,N-diphenyl-2,3-dimethyl-4-methylthio-benzamide.

At most 45° C., 5.7 g (50 mmol) of 30% strength hydrogen peroxide are added dropwise to a solution of 7 g (20 mmol) of N,N-diphenyl-2,3-dimethyl-4-methylthiobenzamide and 200 mg of sodium tungstate hydrate in 50 ml of glacial acetic acid. The reaction mixture is stirred at room temperature overnight. For work-up, the mixture is poured into ice-water and extracted with methylene chloride, and the organic phase is washed with aqueous sodium sulfite solution, dried over magnesium sulfate and concentrated.

Yield: 7.4 g of N,N-diphenyl-2,3-dimethyl-4-methylsulfonyl-benzamide, m.p.: 155–165° C.

b) Preparation of N,N-diphenyl-3-hydroxyimino-2-methyl-4-methylsulfonl-benzamide A solution of 0.7 g (6.9 mmol) of n-butyl nitrite (97% pure) and 2 g (5.3 mmol) of N,N-diphenyl-2,3-dimethyl-4-methylsulfonylbenzamide in 30 ml of dimethylformamide is cooled to from −55 to −60° C., and a solution of 1.4 g (12 mmol) of potassium tert-butoxide in 10 ml of dimethylformamide is added dropwise at this temperature, over a period of 20 minutes. The reaction is monitored by HPLC. For work-up, initially 10 ml of water are added, and the pH is subsequently adjusted to 5–6 using glacial acetic acid. The reaction mixture is subsequently poured into 100 ml of ice-water, and the aqueous phase is extracted with ethyl acetate. The organic phase is washed with sodium bicarbonate solution, dried over magnesium sulfate and concentrated. This gives 3.0 g of a partially crystalline crude product which is purified by silica gel chromatography using toluene/acetone as mobile phase.

Yield: 1.0 g (46%), m.p.: 208–211° C.

EXAMPLE 18

Preparation of 3-bromo-2-methyl-6-methylsulfonylbenzaldehyde 7.1 g of 3-bromo-2-methyl-6-methylsulfonylbenzaldoxime (23 mmol) are stirred in a mixture of 17 g of 5% strength hydrochloric acid, 2 g of a 37% strength solution of formaldehyde, 15 ml of water and 30 ml of tetrahydrofuran at 65° C. for 32 hours. During this time, a further 3.5 g of a 37% strength solution of formaldehyde are added in portions of 0.5 g. The mixture is subsequently cooled to room temperature, and the product is filtered off with suction.

This gives 5.1 g (79%), purity 94% (according to GC)

EXAMPLE 19

Preparation of 2-methyl-6-nitrobenzaldehyde

At 65° C., 14 g of 2-methyl-6-nitrobenzaldoxime (80 mmol) are stirred in a mixture of 55 ml of 5% strength hydrochloric acid, 37 g of a 37% strength solution of formaldehyde, 50 ml of water and 100 ml of tetrahydrofuran for 24 hours. The phases are subsequently separated, and the dark phase is extracted with methylene chloride/water. The organic phase is dried with sodium sulfate and concentrated. This gives 10.1 g of crude product which is purified by filtration over silica gel using toluene as mobile phase.

Yield: 7.2 g (54%)

EXAMPLE 20

Preparation of 2-methyl-6-nitrobenzonitrile

A solution of 16 g (150 mmol) of n-butyl nitrite (97% pure) and 7.7 g (50 mmol) of 3-nitro-o-xylene (97% pure) in 50 ml of dimethylformamide is cooled to from −5 to −10° C., and a solution of 11 g (100 mmol) of potassium tert-butoxide in 50 ml of dimethylformamide is added dropwise at this temperature, over a period of 1.5 hours. The reaction mixture is stirred at room temperature for another 6 days. For work-up, the mixture is poured into ice-water, the pH is adjusted to 1 using hydrochloric acid and the aqueous phase is extracted with ethyl acetate. The organic phase is washed with water, dried over magnesium sulfate and concentrated. This gives 8.2 g of product. The 2-methyl-6-nitrobenzonitrile can be purified by silica gel chromatography using toluene as mobile phase. M.p.: 101–103° C.

In the following working examples, the preparation of thioethers of the formula VIIIa (process step d) is described in more detail:

EXAMPLE 21 a) Comparative Example

The reaction of 2,3-dimethylaniline with dimethyl disulfide and tert-butyl nitrite in methylene chloride as solvent only gives a small amount of the desired product C. The major products identifiable by GC analysis were the dimerization products A and B. The dimer A is also formed in the reaction in an excess of dimethyl disulfide.

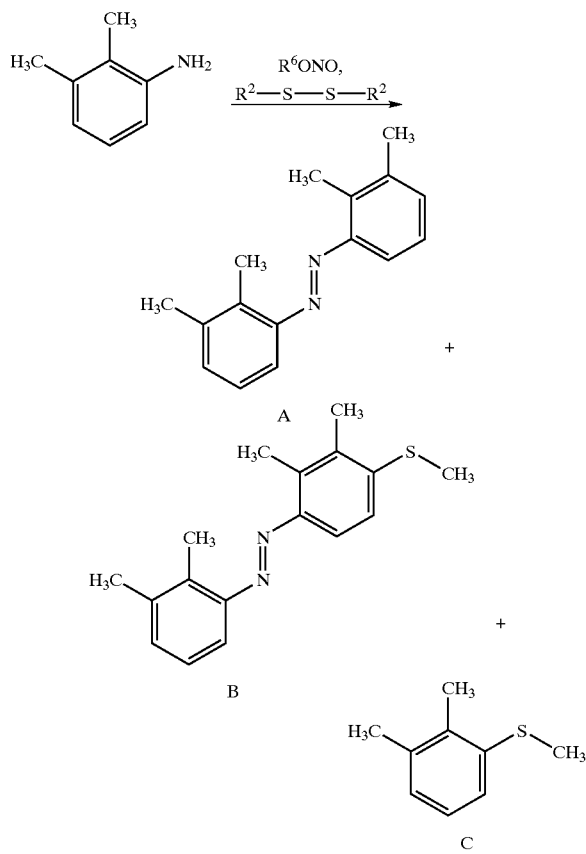

b) Process According to the Invention

Similarly to the method described in a), the reaction of 2,3-dimethylaniline with dimethyl disulfide and tert-butyl nitrite is carried out using the solvent methylene chloride, but Cu powder is additionally added as catalyst. The reaction gives the desired dimethylthioanisole C in a uniform manner. By GC analysis, the dimerization products A and B could not be identified.

EXAMPLE 22 a) Comparative Example

In the reaction of 2-(4,5-dihydroisoxazol-3-yl)-3-methylaniline with dimethyl disulfide and tert-butyl nitrite without catalyst, by-products are formed. A mixture of A and B in a ratio of 2:1 by HPLC area percentage is obtained.

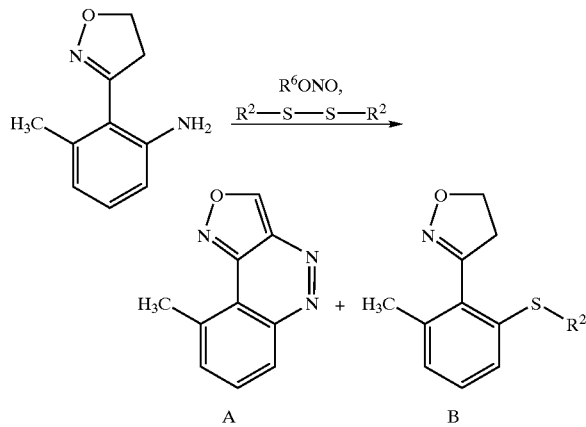

b) Process According to the Invention

Similarly to the method described in a), the reaction is carried out in the presence of Cu powder. In this instance, the by-product A can not be detected.

EXAMPLE 23

Preparation of 2,3-dimethylthioanisole a) 355 g (3.44 mol) of tert-butyl nitrite and 250 g of copper powder (3.9 mol) are initially charged in 1250 ml of dimethyl disulfide, and a solution of 250 g (2.07 mol) of 2,3-dimethylaniline in 1000 ml of dimethyl disulfide is added dropwise at from 50 to 52° C. The mixture is subsequently stirred at from 75° C. to 80° C. for 1.5 hours. For work-up, the mixture is cooled and filtered with suction through diatomaceous earth, and the filtrate is washed with saturated aqueous $NaHCO_3$ solution. For purification of the product, the organic phase is separated by distillation. Initially, the excess dimethyl disulfide is removed at atmospheric pressure. 1446 g of dimethyl disulfide (purity>97% according to GC) are recovered. The residue is subsequently subjected to fractional distillation under reduced pressure (0.1 mbar).

Yield: 261.3 g (83%), purity according to GC 97.5% b) 14.2 g (124 mmol) of tert-butyl nitrite and 2.5 g (40 mmol) of copper powder are initially charged in 50 ml of dimethyl disulfide, and a solution of 10 g (81 mmol) of 2,3-dimethylaniline in 50 ml of dimethyl disulfide is added dropwise at from 50 to 52° C. The mixture is subsequently stirred at from 75 to 80° C. for 1.5 hours. According to GC analysis, 100% of the aniline has been converted into the desired 2,3-dimethylthioanisole.

EXAMPLE 24

Preparation of 2-methyl-6-nitrothioanisole 226 g (1.97 mol) of tert-butyl nitrite and 100 g of copper powder are initially charged in 300 ml of dimethyl disulfide, and a solution of 200 g (1.32 mol) of 2-methyl-6-nitroaniline in 700 ml of dimethyl disulfide is added dropwise at from 50 to 55° C. The mixture is subsequently stirred at 75° C. for 8 hours. For work-up, the solid is filtered off with suction and the filtrate is diluted with methylene chloride and extracted with dilute hydrochloric acid. The organic phase is washed with saturated aqueous $NaHCO_3$ solution, dried over sodium sulfate, filtered off and concentrated. Excess dimethyl disulfide is removed under oil pump vacuum. This gives 271 g (99%) of a dark-red oil, purity according to HPLC 87%.

EXAMPLE 25

Preparation of 2-methyl-3,4-dimethylthiobromobenzene 14.8 g (129 mmol) of tert-butyl nitrite and 20 g of copper powder are initially charged in 50 ml of dimethyl disulfide, and a solution of 20 g (86 mol) of 4-bromo-3-methyl-2-methylthioaniline in 100 ml of dimethyl disulfide is added dropwise at from 50 to 55° C. The mixture is subsequently stirred at 50° C. for 4 hours. For work-up, the solid is filtered off with suction and the filtrate is diluted with methylene chloride and extracted with dilute hydrochloric acid. The organic phase is washed with saturated aqueous $NaHCO_3$ solution, dried over sodium sulfate, filtered off and concentrated. Excess dimethyl disulfide is removed under oil pump vacuum.

This gives 19.7 g of a dark oil. The product can be purified by stirring in methyl tert-butyl ether.

Yield 9.32 g (41%), m.p. 70–73° C.

EXAMPLE 26

Preparation of 2,3-dimethyl-4-methylthiobromobenzene 603 g (5.85 mol) of tert-butyl nitrite and 375 g of copper powder (5.9 mol) are initially charged in 3000 ml of dimethyl disulfide, and 761 g (3.75 mol) of 4-bromo-2,3-dimethylaniline are added dropwise at from 50 to 58° C. The mixture is subsequently stirred at from 75 to 80° C. for 9 hours. For work-up, the mixture is cooled, the residue is filtered off and the filtrate is washed with saturated aqueous NaHCO$_3$ solution. For purification of the product, the organic phase is separated by distillation. Initially, the excess dimethyl disulfide is separated off at atmospheric pressure. 1870 g of dimethyl disulfide (purity>97% according to GC) are recovered. The residue is subsequently subjected to fractional distillation under reduced pressure (0.1 mbar).

Yield: 523 g (60%), purity according to GC 99%.,

EXAMPLE 27

(Reaction Sequence According to Scheme 4)

a) Preparation of 2,3-dimethylthioanisole 355 g (3.44 mol) of tert-butyl nitrite and 250 g of copper powder (3.9 mol) are initially charged in 1250 ml of dimethyl disulfide, and a solution of 250 g (2.07 mol) of 2,3-dimethylaniline in 1000 ml of dimethyl disulfide is added dropwise at 50–52° C. The mixture is subsequently stirred at 75–80° C. for 1.5 hours. For work-up, the mixture is cooled, filtered off with suction through kieselguhr, and the filtrate is washed with saturated aqueous NaHCO$_3$ solution. For the purification of the product, the organic phase is separated by distillation. Initially, excess dimethyl disulfide is removed at atmospheric pressure. 1446 g of dimethyl disulfide (purity>97% according to GC) are recovered. The residue is then subjected to fractional distillation under reduced pressure (0.1 mbar).

Yield: 261.3 g (83%), purity (according to GC) 97.5% b) Preparation of 2,3-dimethyl-4-methylthiobromobenzene 510 g (3.33 mol) of 2,3-dimethylthioanisole are initially charged in 3 l of glacial acetic acid, and a solution of 592 g (7.4 mol) of bromine in 1 l of glacial acetic acid is added dropwise at room temperature over a period of three hours. The reaction is slightly exothermic. The reaction mixture is stirred at room temperature for another 3.5 hours. The precipitate is then filtered off with suction and the filtrate is admixed with 270 g of sodium acetate and concentrated. The residue is taken up in 2 l of dichloromethane and washed twice with 2 l of sodium bicarbonate solution and twice with sodium chloride solution. The organic phase is dried over sodium sulfate and concentrated.

Yield: 615 g (79%), purity (according to GC) 99.2%.

c) Preparation of 2,3-dimethyl-4-methylsulfonylbromobenzene

At most 100° C. (slight reflux), 266 g (2.35 mol) of 30% strength hydrogen peroxide are added dropwise over a period of 45 minutes to a solution of 182 g (0.78 mol) of 2,3-dimethyl-4-methylthiobromobenzene and 5.24 g of sodium tungstate hydrate in 1 l of glacial acetic acid. The reaction mixture is stirred at room temperature for another two hours. For work-up, the mixture is poured onto 7.8 l of ice-water and stirred for another 30 minutes. The white residue is then filtered off with suction and washed three times with water. The crystals are dried at 70° C. under reduced pressure overnight.

Yield: 195 g (94%), purity (according to GC) 100%.

d) Preparation of 3-bromo-2-methyl-6-methylsulfonylbenzaldoxime 272.6 g of sodium ethoxide (3.8 mol) are dissolved in 0.4 l of DMF, and a solution of 400 g of 2,3-dimethyl-4-methyl-sulfonylbromobenzene (1.52 mol) and 214.6 g (1.977 mol) of n-butyl nitrite in 0.8 l of DMF is added at from −20° C. to −15° C. Subsequently, another 100 g of sodium ethoxide are added. The reaction mixture is stirred at from −20° C. to −15° C. for a total of 5.5 hours.

The mixture is poured onto 4 l of ice-water and 0.4 l of glacial acetic acid and extracted with a total of 4 l of MtBE. The MtBE phase is washed with 1 l of sodium bicarbonate solution and twice with water. The aqueous phases are combined. The MtBE phase is concentrated using a rotary evaporator and dried. The solution is concentrated and the residue is dried using an oil pump.

Yield: 331 g (75%) of yellow-brown crystals, purity (according to HPLC) 96.6%.

e) Preparation of 3-(3-bromo-2-methyl-6-methylsulfonylphenyl)-4,5-dihydro-isoxazole At 60° C., a small amount of N-chlorosuccinimide is added to a solution of 50 g (171 mmol) of 3-bromo-2-methyl-6-methyl-sulfonylbenzaldoxime in 200 ml of dimethylformamide. Once the reaction has started, a total of 23.3 g (171 mmol) of N-chlorosuccinimide are metered in at 40–50° C. The reaction mixture is stirred for another 30 minutes, until conversion is complete according to HPLC. The reaction mixture is then poured onto ice-water and the solid is filtered off with suction, washed three times with water and twice with n-pentane. The hydroxamic acid chloride is used moist and without further purification for the next reaction. The solid is dissolved in 250 ml of dichloromethane, and ethylene is passed through the solution. With continued introduction of ethylene, 20.3 g (200 mmol) of triethylamine are added dropwise. The reaction mixture is stirred at room temperature for about 72 hours, with repeated introduction of more gaseous ethylene.

For work-up, the reaction mixture is washed three times with water, and the solvent is stripped off. This gives 49 g of brownish crystals which, according to HPLC, contain 90.6% of product. The product can be purified by recrystallization from 200 ml of isopropanol.

Yield: 31 g (57%) of white crystals, m.p.: 133–136° C., purity (according to HPLC) 99.5%.

What is claimed is:

1. A compound of the formula XII

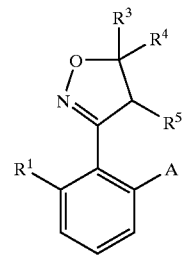

XII where:

A is a group —S—R$^2$;

R$^1$ is hydrogen, C$_1$–C$_6$-alkyl;

R$^2$ is hydrogen;

R$^3$, R$^4$, R$^5$ are each hydrogen, C$_1$–C$_6$-alkyl or R$^4$ and R$^5$ together form a bond.

* * * * *